(12) United States Patent
Sowerby

(10) Patent No.: US 8,961,907 B2
(45) Date of Patent: Feb. 24, 2015

(54) APPARATUS FOR THE DETECTION AND ANALYSIS OF PARTICLES IN FLUIDS

(75) Inventor: Stephen John Sowerby, Dunedin (NZ)

(73) Assignee: Menixis Limited, Dunedin (NZ)

( * ) Notice: Subject to any disclaimer, the term of this patent is extended or adjusted under 35 U.S.C. 154(b) by 146 days.

(21) Appl. No.: 13/387,076

(22) PCT Filed: Jul. 22, 2010

(86) PCT No.: PCT/NZ2010/000151
§ 371 (c)(1),
(2), (4) Date: Jan. 25, 2012

(87) PCT Pub. No.: WO2011/014079
PCT Pub. Date: Feb. 3, 2011

(65) Prior Publication Data
US 2012/0135457 A1    May 31, 2012

(30) Foreign Application Priority Data

Jul. 28, 2009 (NZ) ........................... 578644
Aug. 28, 2009 (NZ) ........................... 579316

(51) Int. Cl.
*B01L 3/00* (2006.01)
*G01N 21/03* (2006.01)
*G01N 15/14* (2006.01)

(52) U.S. Cl.
CPC ............ *G01N 21/03* (2013.01); *B01L 3/5088* (2013.01); *G01N 15/1484* (2013.01); *B01L 2200/0668* (2013.01); *B01L 2300/0832* (2013.01); *B01L 2300/0851* (2013.01); *G01N 21/0303* (2013.01); *G01N 2021/035* (2013.01)
USPC ......... 422/551; 422/549; 422/559; 435/305.1

(58) Field of Classification Search
USPC ........... 422/73, 549, 551, 552, 553, 557, 559; 435/305.1; 73/864.61
See application file for complete search history.

(56) References Cited

U.S. PATENT DOCUMENTS 6,588,266 B2 * 7/2003 Tubel et al. ................ 73/152.39
2003/0091979 A1 * 5/2003 Eschenhagen .................... 435/4

FOREIGN PATENT DOCUMENTS

| CH | 637209 | 7/1983 |
| JP | 07-120454 | 5/1995 |

* cited by examiner

Primary Examiner — Jill Warden
(74) Attorney, Agent, or Firm — Blakely Sokoloff Taylor & Zafman LLP

(57) ABSTRACT

The invention relates to apparatus for the detection of particles and for particle analysis. The apparatus comprises a sample holder comprising a base and a projection extending from the base. The base includes a contact region where, in use, the surface of a fluid sample may contact the projection. The surface of at least the contact region of the projection exhibits properties that allow the surface of the contact region to be substantially wetted by a fluid sample when the apparatus is in use so that the fluid sample forms a meniscus having its apex in contact with the contact region of the projection. The invention also relates to methods for using the apparatus.

19 Claims, 14 Drawing Sheets

APPARATUS FOR THE DETECTION AND ANALYSIS OF PARTICLES IN FLUIDS

CROSS-REFERENCE TO RELATED APPLICATION

The present patent application is a national phase application of International Application No. PCT/NZ2010/000151, filed Jul. 22, 2010.

FIELD OF THE INVENTION

The invention relates to an apparatus adapted to allow a user to detect the presence of particles suspended in fluids and to identify and analyse those particles. The invention also relates to a method of using the apparatus.

BACKGROUND TO THE INVENTION

The determination of the presence, type, and number of parasites is relevant to human and animal health. In particular, the detection of parasite eggs can indicate an undesirable parasitic infection in the human or animal host. Microscopy is commonly used to detect, identify, and count parasite eggs within different materials, especially biological materials that include: feaces; drinking water; waste water; soil; blood; and food for example.

It may also be important to determine the presence, type, and number of other particles in materials such as water, soil, and food to assess contamination of the material. For example, the presence, type, and number of pollen particles in a sample of soil may be used in scientific or archaeological studies. Similarly, the presence, type, and number of pollen particles in honey may be used to determine the type of honey.

Consequently, various apparatus and methods have been developed that use microscopy for detecting, identifying, and counting sub-millimeter scale particles within material suspended in a fluid sample, such particles including pollen and parasite eggs for example.

However, a difficulty associated with the microscopic analysis of some materials in fluids is that the particles tend to be positioned throughout the fluid and also tend to move within the fluid. As a result, the particles do not accumulate or remain within the same microscopic field of view or within a common focal plane. The microscope operator is, therefore, required to translate the microscope and adjust its focal point to view all particles dispersed throughout the sample.

One known device and method of particle analysis has attempted to overcome this difficulty by providing for a sample of the particles to be examined on a microscope slide called a McMaster slide. The slide includes upper and lower transparent plates with a cavity between. This device and method requires the use of a compound optical microscope. In this form of particle analysis, the buoyant particles float to the surface of a dense fluid sample. A sample of the fluid is taken and placed within the cavity of the slide. The particles in the slide are substantially immobilised and fixed within a common focal plane as a result of buoyant forces and the upper plate of the slide. An operator uses a microscope to manually observe and identify the particles. However, the device and method do not bring the particles within a single microscopic field of view. Thus, the area of the slide that can be simultaneously observed is limited so it becomes necessary for the microscope operator to continually translate the microscope over the slide to detect and/or identify and/or count particles on the slide. Also, the slide must be handled with great care to prevent the contents of the slide from spilling out.

Another method and device specifically used for the detection, identification, and/or counting of parasite eggs from the faecal stool samples of agricultural livestock and humans is called FLOTAC (see Cringoli et al., "FLOTAC: New multivalent techniques for qualitative and quantitative copromicroscopic diagnosis of parasites in animals and humans", Nature Protocols, 5, 503-515, 2010). The FLOTAC device and method can be used to analyse the presence of helminth parasites in the stool specimens of various species of animals, including humans, by providing for the detection, identification, and/or counting of parasite eggs in the stool specimens.

However, each of these known devices and methods for particle detection, identification, and analysis exhibit a number of disadvantages.

One disadvantage is that the presence of pigments and debris in the fluid samples limits the depth of the sample that can be analysed, due to the difficulty of viewing particles in such samples.

Another disadvantage is that only operators with a sufficient level of competency can carry out the analysis using such sophisticated devices as compound optical microscopes, thereby often limiting the analysis to a laboratory environment.

Yet another disadvantage is that the field of view offered by a compound optical microscope (operated at sufficient magnification to enable particle detection, identification, and counting), limits the area that can be simultaneously observed and, therefore, requires the microscope operator to translate the field of view over a specified area of the sample.

The process of manual translation of the microscope is time-consuming, adding to the cost of the analysis. Translation also introduces vibrations which may lead to inaccuracies in the analysis of particles. In addition, the prolonged viewing of a moving image causes eye strain and fatigue, and repeated manual operations of adjustment can cause repetitive strain injury (RSI).

Furthermore, it is desirable to be able to audit the raw data and analysis of the image data because of the risk of misidentification. Such permanent records often take the form of optical photomicrographs, which can be procured in a digital format and allow for their electronic storage and communication. However, the requirement for translation diminishes the practicability of recording the microscope image data because multiple overlapping image frames must be captured and stored in order to view the whole slide.

Thus, there is a need to provide an apparatus and method for the microscopic analysis of particles in fluids that: (a) positions the particles in a common focal plane; (b) reduces the need to translate the microscope to view the sample; (c) mitigates the effects of pigmentation and extraneous debris; (d) improves the practicability of providing a permanent record of the microscope image data; (e) can be operated outside of a laboratory by relatively unskilled people; or (f) at least provides the public with a useful alternative.

SUMMARY OF THE INVENTION

The term "analysing particles", as used in this specification and claims, means detecting the presence of particles, identifying the type of particles, or counting the number of particles.

The term "fluid wettable", as used in this specification and claims, means that the fluid wettable surface has properties that will cause the meniscus of a fluid in contact with that surface to form a contact angle, of less than 90°. The contact angle is the angle between the tangent of the meniscus (at the point of contact with the fluid wettable surface) and the fluid wettable surface.

The term 'material', as used in this specification and claims, refers to solid or liquid matter that is to be analysed to test the presence of particles and/or the type of particles and/or to count the particles in the matter.

The term 'fluid sample', as used in this specification and claims, refers to a sample of fluid that includes material thought to include particles to be detected and/or analysed. For example, the fluid sample may be formed from a solid material mixed into a fluid to form the fluid sample. Alternatively, the fluid sample may be formed from a liquid material mixed with another fluid to form the fluid sample. Alternatively, the fluid sample may be a sample of a liquid itself, such as a sample of water, a beverage, or liquid honey for example. Fluid in a fluid sample has a specific gravity higher than the specific gravity of any particles intended to be detected, identified by their type, or counted in the fluid sample. For example, the sample material may be added to a fluid, such as sodium nitrate, sucrose, magnesium sulphate, zinc sulphate, or sodium chloride, or any other fluid having a higher specific gravity than the samples being tested.

According to a first aspect the invention provides an apparatus for the detection of particles and for particle analysis, the apparatus comprising a sample holder comprising a base and a projection, the projection comprising: a bottom end supported by the base, such that the projection extends from the base, a contact region where, in use, the surface of a fluid sample may contact the projection; and the projection also comprising a distal end, wherein the surface of at least the contact region of the projection exhibits properties that allow the contact region to be substantially wetted by a fluid sample when the apparatus is in use so that the fluid sample forms a meniscus having its apex in contact with the contact region of the projection.

Preferably, the surface of at least the contact region of the projection exhibits properties that make the contact region hydrophilic, superhydrophilic, oleophilic, or fluorophilic.

In a preferred form, the distal end of the projection is tapered. The contact region is located at the distal end of the projection and may or may not include the tip of the projection.

Preferably, the sample holder further comprises a wall or walls extending from the base and equidistant from the projection. The base and wall(s) together form a fluid cavity. The projection is positioned substantially centrally within the fluid cavity and the wall(s) comprise inner surfaces facing the fluid cavity. The inner surfaces of the wall(s) exhibit properties that cause the wall(s) to substantially repel a fluid sample when the apparatus is in use so that the fluid sample forms a meniscus having its apex in contact with the projection. Preferably, the inner surfaces of the wall(s) are hydrophobic, superhydrophobic, oleophobic, or fluorophobic.

The wall(s) of the fluid cavity may terminate in a free edge, which is chamfered to form a surface that slopes outwardly toward the base of the sample holder.

Preferably, the base of the fluid cavity is substantially concave.

Preferably, the sample holder comprises illuminating means to illuminate at least a portion of a fluid sample held by the sample holder when the apparatus is in use. Optionally, the projection is adapted to provide a light transmitting conduit to illuminate at least a portion of a fluid sample held by the sample holder when the apparatus is in use. Most preferably, at least the contact region of the projection is substantially transparent or translucent to transmit light to at least the area immediately surrounding the contact region. Alternatively, substantially the entire projection may be substantially transparent or translucent to transmit light to at least the area immediately surrounding the projection.

The apparatus may further comprise viewing means to assist a user to view any particles present in a fluid sample held by the sample holder when the apparatus is in use. Optionally, the projection comprises a plurality of fibre optic cables and the viewing means comprises an image sensor coupled to the fibre optic cables. Optionally, the image sensor is configured to capture an image of at least the area above and immediately surrounding the distal end of the projection and transmit this image to a display or storage device to display or store the image.

According to a second aspect, the invention provides a method for analysing particles in a fluid sample using the apparatus of the invention. The method comprises the following steps: (a) placing a volume of fluid sample onto the base of the apparatus so that the fluid sample forms a meniscus with its apex contacting the contact region of the projection; (b) waiting for a period of time for any buoyant particles in the fluid to ascend through the fluid and accumulate at or near the apex of the meniscus; and (c) viewing a region comprising at least the surface of the fluid sample at and around the apex of the meniscus to determine the presence of any particles and/or to analyse particles within this region.

Preferably, the contact region of the projection is located at the distal end of the projection, the distal end being tapered, and wherein the apex of the meniscus is proximate to the apex of the tapered distal end of the projection.

Preferably, the fluid sample is illuminated by light transmitted through the base of the apparatus, through the projection, or through both. More preferably, the fluid sample is illuminated by light emitted through at least the distal end of the projection.

In another preferred form, at least a portion of the fluid sample is captured as an image and transmitted to a display device for viewing and storage.

According to a third aspect, the invention provides an apparatus for the detection of particles and for particle analysis, the apparatus comprising a sample holder comprising a base and a projection, the projection comprising: a bottom end supported by the base, such that the projection extends from the base, and a distal end; wherein the apparatus is adapted so that, in use, a fluid sample forms a convex meniscus having its apex substantially above the distal end of the projection and the apparatus is further adapted to illuminate, from below, at least a portion of a fluid sample placed on the sample holder when the apparatus is in use.

Preferably, the sample holder comprises illuminating means to illuminate at least a portion of a fluid sample held by the sample holder when the apparatus is in use. Optionally, the projection is adapted to provide a light transmitting conduit to illuminate at least a portion of a fluid sample held by the sample holder when the apparatus is in use. Most preferably, at least the distal end of the projection is substantially transparent or translucent to transmit light to at least the area immediately surrounding the contact region. Alternatively, substantially the entire projection may be substantially transparent or translucent to transmit light to at least the area immediately surrounding the projection.

Preferably, the sample holder further comprises a wall or walls extending from the base and equidistant from the projection. The base and wall(s) together form a fluid cavity. The projection is positioned substantially centrally within the fluid cavity and the wall(s) comprise inner surfaces facing the fluid cavity.

The wall(s) of the fluid cavity may terminate in a free edge, which is chamfered to form a surface that slopes outwardly toward the base of the sample holder.

Preferably, an upper surface of the base of the fluid cavity is substantially concave.

The apparatus may further comprise viewing means to assist a user to view any particles present in a fluid sample held by the sample holder when the apparatus is in use. Optionally, the projection comprises a plurality of fibre optic cables and the viewing means comprises an image sensor coupled to the fibre optic cables. Optionally, the image sensor is configured to capture an image of at least the area above and immediately surrounding the distal end of the projection and transmit this image to a display or storage device to display or store the image.

In a fourth aspect, the invention provides a method for analysing particles in a fluid sample using the apparatus of the invention. The method comprises the following steps: (a) placing a volume of fluid sample onto the base of the apparatus so that the fluid sample forms a convex meniscus with its apex substantially above the distal end of the projection of the apparatus; (b) waiting for a period of time for any buoyant particles in the fluid to ascend through the fluid and accumulate at or near the apex of the meniscus; and (c) viewing a region comprising at least the apex of the meniscus to determine the presence of any particles and/or to analyse particles within this region.

Preferably, the fluid sample is illuminated by light transmitted through the base of the apparatus, through the projection, or through both. More preferably, the fluid sample is illuminated by light transmitted through at least the distal end of the projection.

In another preferred form, at least a portion of the fluid sample is captured as an image and transmitted to a display device for viewing and storage.

In a fifth aspect, the invention provides an apparatus for the detection of particles and for particle analysis, the apparatus comprising a rod having a base portion and a projection extending from the base portion, wherein the projection comprises a distal end and a contact region where, in use, the surface of a fluid sample may contact the projection; and wherein the surface of at least the contact region of the projection exhibits properties that allow the contact region to be substantially wetted by a fluid sample when the apparatus is in use so that the fluid sample forms a meniscus having its apex in contact with the contact region of the projection.

Preferably, the surface of at least the contact region of the projection exhibits properties that make the contact region hydrophilic, superhydrophilic, oleophilic, or fluorophilic.

In a preferred form, the distal end of the projection is tapered. The contact region is located at the distal end of the projection and may or may not include the tip of the projection.

Preferably, the base portion of the rod comprises a fluid repelling region. This region may exhibit properties that make it hydrophobic, superhydrophobic, oleophobic, or fluorophobic.

Preferably, the sample holder comprises illuminating means to illuminate at least a portion of a fluid sample held by the sample holder when the apparatus is in use. Optionally, the projection is adapted to provide a light transmitting conduit to illuminate at least a portion of a fluid sample surrounding the projection when the apparatus is in use. Most preferably, at least the contact region of the projection is substantially transparent or translucent to transmit light to at least the area immediately surrounding the contact region. Alternatively, substantially the entire projection may be substantially transparent or translucent to transmit light to at least the area immediately surrounding the projection.

The apparatus may further comprise viewing means to assist a user to view any particles present in a fluid sample held by the sample holder when the apparatus is in use. Optionally, the projection comprises a plurality of fibre optic cables and the viewing means comprises, an image sensor coupled to the fibre optic cables. Optionally, the image sensor is configured to capture an image of at least the area above and immediately surrounding the distal end of the projection and transmit this image to a display or storage device to display or store the image.

BRIEF DESCRIPTION OF THE DRAWINGS

Embodiments of the invention will now be described, by way of example only, with reference to the accompanying drawings in which.

DETAILED DESCRIPTION OF PREFERRED FORMS OF THE INVENTION

The invention provides an apparatus and method for analysing particles in a fluid sample to detect and/or identify and/or count buoyant particles. The fluid in the fluid sample is a dense fluid, which means that it has a density greater than the density of the particles to be analysed, thereby allowing the particles to float in the dense fluid.

Figure 1:
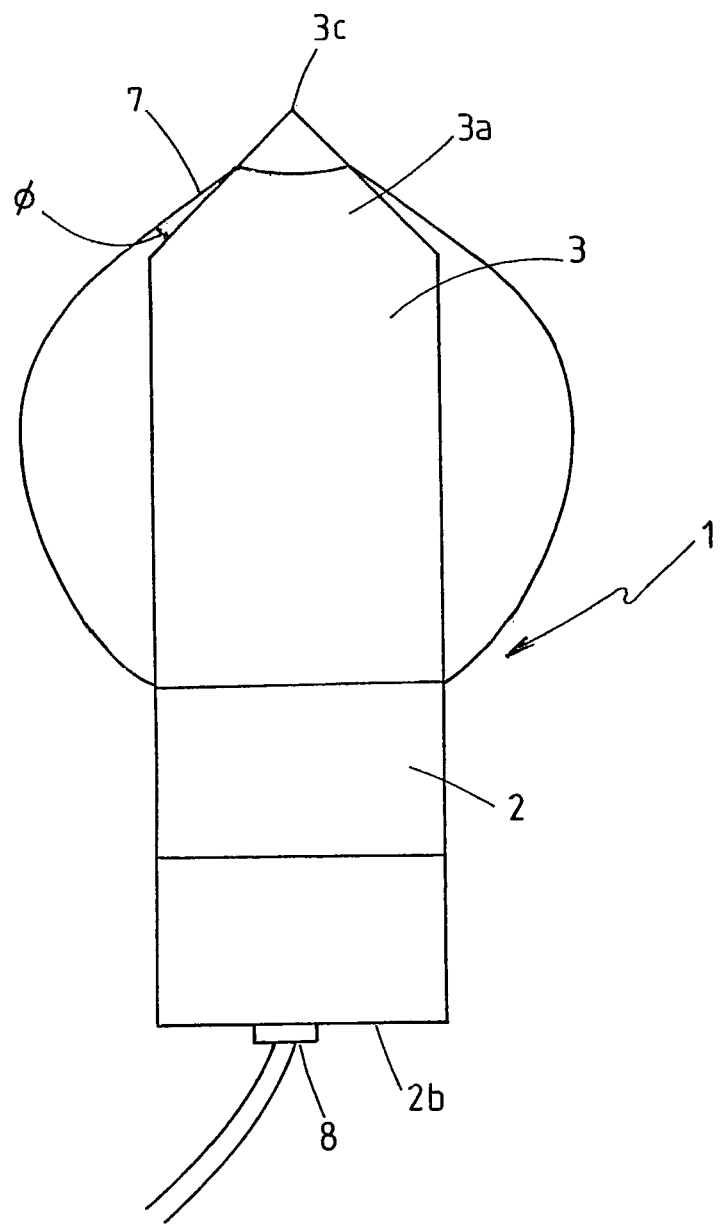
FIG. 1 shows a side view of one embodiment of the invention in use.

In one embodiment shown in FIG. 1, the apparatus comprises a sample holder in the form of a rod 1 comprising a base portion 2 and a projection 3. However, it is envisaged that the sample holder may take other forms and is not limited to taking the form of a rod.

The projection 3 includes a bottom end supported by the base portion 2 such that the projection extends from the base portion 2. Preferably, the projection and base portion are formed from a single part so as to be integral with each other. The projection includes a distal end 3a with a tip 3c positioned substantially opposite the base. The distal end of the projection is preferably tapered, as shown in FIG. 1, although the distal end may, alternatively, be blunt, with a substantially flat apex or tip. The tapered distal end may be conical, hemispherical, stepped, frustoconical, or of any other suitable form. Alternatively, the entire surface of the projection and base may be tapered. For example, the projection and base may together form a cone, pyramid, or the like.

In one form, the projection comprises a substantially fluid wettable contact region where, in use, the fluid sample substantially wets the contact region and forms a meniscus having an apex that contacts the contact region of the projection. The contact region of the projection is preferably located at the distal end of the projection and may or may not include the tip of the projection.

At least the contact region at the distal end of the projection is formed from or coated with a material, or includes a textured surface, that allows the substantially fluid wettable projection to exhibit properties that allow the surface of the contact region to be substantially wetted by a fluid sample when the apparatus is in use so that the fluid sample forms a meniscus having its apex in contact with the projection.

Preferably, the contact region at the distal end has hydrophilic, super-hydrophilic, oleophilic, or fluorophilic properties. Alternatively, the whole of the projection exhibits one of these properties. In use, a user selects an apparatus having a projection with properties that will allow at least the contact region of the projection to be substantially wetted by the analyte fluid used in the fluid sample so that the fluid forms a meniscus with its apex in contact with the contact region. For example, if the analyte fluid is oil-based, the contact region should be oleophilic. Similarly, if the analyte fluid is water-based, the contact region should be hydrophilic or superhydrophilic. If the analyte fluid is fluorocarbon-based, the contact region should be fluorophilic.

The base of the apparatus shown in FIG. 1 includes at least one fluid repelling region. The fluid repelling region forms a collar surrounding the periphery of the projection in a substantially horizontal plane. The collar may enclose the entirety of the base portion or it may be located between the distal end of the projection and the bottom surface 2b of the base. The base portion is formed from or coated with a material, or includes a textured surface, that provides the sample holder portion with fluid repelling properties, such as hydrophobic, super-hydrophobic, oleophobic, or fluorophobic properties. Again, the properties of the base that are desired depend on the analyte fluid used in the fluid sample.

The apparatus may optionally further include at least one illuminating means 8, as shown in FIG. 1. The illuminating means allows a user to more easily view particles in at least the region of fluid immediately surrounding the contact region at the distal end of the projection by illuminating this region. The at least one illuminating means may be selected from the group comprising, but not limited to: lights; lamps; bulbs; lasers; light emitting diodes (LEDs); laser diodes; cameras; fibre optic cables; lenses; microscopes; or any other suitable component.

Optionally, the projection is adapted to illuminate the fluid sample to allow particles to be more easily detected, identified, and counted. In this form, at least the distal end of the projection is formed of substantially transparent or translucent material. Preferably, the entire projection is formed from such light transmitting material so as to be transparent or translucent. The projection, therefore, provides a conduit through which a light source can transmit or project light to illuminate at least a portion of the region surrounding and including the distal end of the projection, especially the region in which the fluid meniscus contacts the projection or where the fluid surface sits above the projection when the apparatus is in use.

The light source may be housed within the projection or within the base of the sample holder or apparatus. Alternatively, the light source may be located external to the sample holder or apparatus and connected to the projection to allow light to be transmitted from the light source to the distal end of the projection or to a point near the distal end of the projection.

Substantially the whole projection, or at least its distal end, may be fabricated of any light transmitting solid material, such as, but not limited to: polymers; acrylic; polycrystalline solids; and glass, especially borosilicate glass The apparatus may further comprise viewing means to capture images of the apparatus and of the fluid sample. The viewing means may be positioned above, below, or at the side of the apparatus. Similarly, images of the apparatus and fluid sample captured by the viewing means may be taken from above, below, or from the side of the apparatus.

Preferably, the viewing means is in the form of an image sensor. In this form, the projection is formed of a plurality of fibre optic cables coupled to an image sensor. The image sensor may be a CCD sensor or CMOS sensor, or any other suitable image sensor from which an image of the fluid sample immediately surrounding the distal end of the projection can be captured and transmitted to a display device for viewing and, optionally storing for reference or auditing at a later date.

In one method of using the apparatus of the invention, a volume of the fluid sample to be analysed is placed on the contact region at the distal end of the apparatus by any suitable method, such as by using a pipette to add the fluid to the distal end, or by dipping the projection of the apparatus into the fluid sample. The properties of the fluid sample and the contact region of the substantially fluid wettable projection are such that the fluid sample wets the contact region of the projection and forms a droplet about the distal end. The fluid sample forms a fluid meniscus, having its apex substantially in contact with the contact region of the projection. Preferably, the apex of the meniscus is located proximate to the apex of the tapered distal end 3a of the projection 3. This arrangement causes buoyant particles within the fluid sample to float toward the apex of the meniscus and accumulate around the projection, preferably in a single microscopic field of view. Upon contact with the projection, the buoyant particles are substantially immobilised as a result of adhesive forces.

Figure 2:
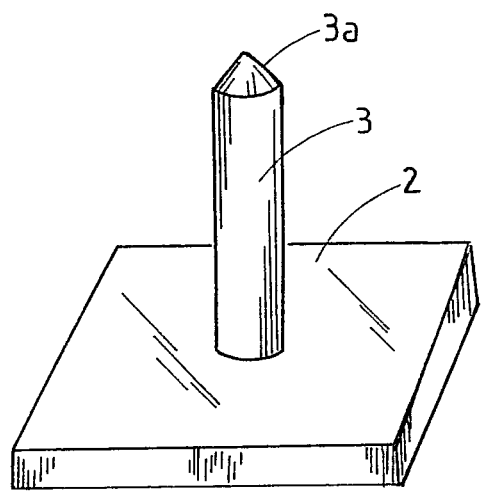
FIG. 2 shows a perspective view of another embodiment of the invention.

In another form of the invention, as shown in FIG. 2, the apparatus comprises a sample holder comprising a base 2 having an upper surface, and further comprising a projection 3 having a bottom end supported by the base so that the projection extends from the base 2. The projection also comprises a distal end 3a. The projection 3 comprises a substantially fluid wettable contact region that has a textured surface, or is made from or coated with a material, that will cause the projection to be substantially wetted by the fluid sample to be analysed by the apparatus. For example, the projection may have a textured surface, or may be made from or coated with a material, that causes the projection to be hydrophilic, super-hydrophilic, oleophilic, or fluorophilic.

Figure 3:
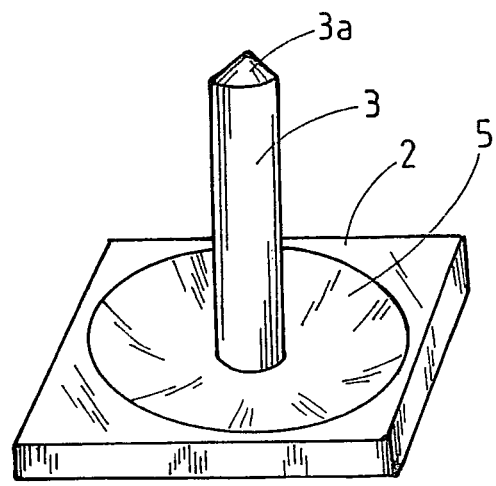
FIG. 3 shows a perspective view of another embodiment of the invention.

The base of the apparatus may be substantially flat, as shown in FIG. 2. Alternatively, as shown in FIG. 3, the upper surface of the base 2 may comprise a concave portion surrounding the projection 3 so that the concave portion forms a fluid cavity 5 upon which a volume of sample fluid will be held when the apparatus is in use.

The distal end 3a of the projection is tapered with a tip 3c. The tapered distal end of the projection may be, for example, hemispherical, conical or frustoconical, as shown in FIGS. 14a to 14f. Alternatively, the distal end may have a substantially flat tip. Alternatively the entire projection, or substantially the entire projection may be tapered. In each embodiment, the projection has a sealed distal end.

The contact region is located at the distal end of the projection and may or may not include the tip of the projection.

In one form, the apparatus further comprises at least one illuminating means to allow a user to more easily view particles in the region of fluid immediately surrounding the contact region of the projection by illuminating this region when the apparatus is in use.

The at least one illuminating means may be selected from the group comprising, but not limited to: lights; lamps; bulbs; lasers; light emitting diodes (LEDs); laser diodes; cameras; fibre optic cables; lenses; microscopes; or any other suitable component.

In a preferred form, at least the distal end of the projection is formed from light transmitting material and, a light source projects through the distal end of the projection. Alternatively, the entire projection is formed from light transmitting material so as to be transparent or translucent. Thus, the projection acts as a conduit for light to illuminate at least a portion of the region surrounding and including the contact region of the projection.

As described above, the apparatus may include at least one viewing means to allow a user to view particles in the region of the fluid sample that at least immediately surrounds the distal end of the projection or that lies above the distal end of the projection. The viewing means may be positioned above, below, or at the side of the apparatus. Similarly, images of the apparatus and fluid sample may be captured by the viewing means from above, below, or from the side of the apparatus.

The viewing means optionally operates by transmitting at least one image of the region to a display device (such as a printer, or display screen or the like) or to an image storage device where the image can be recorded and stored for viewing at a later time.

The at least one viewing means may be selected from one or more of the group comprising, but not limited to: cameras; microscopes; digital image sensors, such as charge coupled device (CCD) sensors or complementary metal oxide semiconductor (CMOS) sensors for example; analogue image sensors; computer screens; personal digital assistants (PDAs) having a display screen; telephones, including mobile telephones and radiotelephones having a display screen; and other suitable image display devices.

In one form, the projection comprises a plurality of optical fibres fused together to form the projection. In this form, the projection provides a conduit along which images can be transmitted from the contact region at the distal end of the projection to image the region of the fluid sample immediately surrounding the contact region of the projection when the apparatus is in use. The plurality of optical fibres forming the projection are coupled to a viewing means comprising an image sensor.

The image sensor is located at the base of the projection to monitor the region surrounding and including the distal end of the projection. The image sensor is also coupled to an image storage device and/or display device that displays the image captured by the image sensor to allow a user to view the image to detect and/or identify and/or count particles.

In a preferred form, the image sensor comprises a CCD or CMOS image sensor that captures the image of the fluid sample in at least the region immediately surrounding the contact region of the projection when the apparatus is in use.

The viewing means may form part of the apparatus or the viewing means may be an external device that is used together with the apparatus of the invention to view any particles present within the fluid sample tested.

To help provide a clear image of any particles above or surrounding the distal end of the projection, the fluid sample may be illuminated from above or from the side by illuminating means, such as a light source integral with the apparatus or an external light source. Alternatively, the fluid sample may be illuminated from below or the side by light emitted from the projection, or from below by light emitted from the base of the fluid cavity. Where light is emitted from the base of the fluid cavity, the base comprises a light transmitting region, which may be transparent or translucent, through which light is projected. The captured image can then be transmitted to an image storage or display device to store or display the recorded image for subsequent examination, such as for the detection and/or identification and/or counting of particles.

The storage or display device may be selected from the group comprising, but not limited to: visual display units; computers; liquid crystal displays; plasma displays; cathode ray tubes; printers; personal digital assistants (PDAs); computer networks, including the internet; telephones, including mobile telephones and radiotelephones; transmitters; transceivers; global positioning system (GPS) enabled devices; and other suitable image recording, transmitting and/or display devices.

One method of using the apparatus shown in FIGS. 2 and 3, is as follows. The apparatus is oriented so that the base is substantially horizontal. The sample holder is then loaded with a pre-prepared metered volume of a fluid sample. The fluid may be of sufficient volume to allow the surface of the fluid sample to contact the contact region at the distal end of the projection and form a meniscus having its apex positioned against the contact region of the projection.

The fluid sample is then left for a period of time to allow buoyant particles to ascend through the fluid and accumulate at or near the apex of the meniscus.

If the volume of fluid is such that the apex of the meniscus contacts the projection, as shown in FIGS. 14b to 14f, then the particles will accumulate at and near the contact line, where the surface of the fluid contacts the projection. The substantially fluid wettable contact region of the projection is wetted by the fluid so that, at the contact line, the contact angle Ø of the liquid with the distal end of the projection is preferably less than 90°, less than 60°, less than 30°, less than 10°, less than 5°, or less than 1°.

Upon contact with the projection, the particles accumulate and, due to the capillary adhesive forces between the projection and the particles, the particles become substantially immobilised at the point of contact with the projection.

Figure 14A:
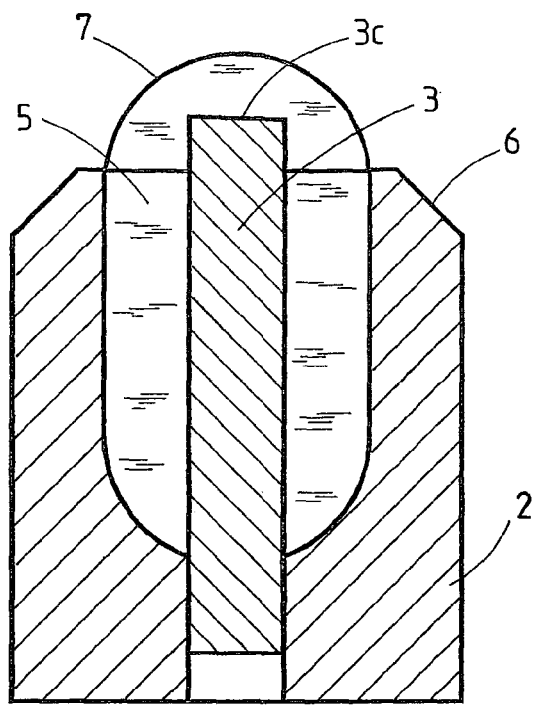
FIGS. 14a to 14f are cross-sectional views of various embodiments of the apparatus of the invention and examples of the different shapes of meniscus that can be formed when the various apparatus are used.

Alternatively, the volume of fluid may be such that it forms a convex meniscus that surrounds the projection, as shown in FIG. 14a. Thus, the projection of the apparatus lies completely below the surface of the fluid sample. Buoyant particles accumulate at the peak or apex of the meniscus, which is located above the projection. In this form, the apex or crown of the meniscus preferably aligns vertically with the projection. The distal end of the projection acts as a false floor or shelf to form a region of reduced fluid depth between the surface of the fluid and the surface of the distal end. By reducing the depth of the fluid sample, particles in a fluid sample (especially a sample that is heavily pigmented or that includes debris) are more easily visible. The depth may be less than 10 mm, less than 5 mm, less than 2 mm, less than 1 mm, or less than 0.1 mm.

The fluid sample and particles may optionally be illuminated by a light source from above and/or at the side of the apparatus. Alternatively, or additionally, the fluid sample and particles may be illuminated by a light source projecting from the base, and/or from a light source projecting through the projection.

Where the entire projection lies below the surface of the fluid sample so that the projection acts as a false floor to reduce the depth of fluid above its distal end, the projection can illuminate the region of fluid having a reduced depth. This arrangement is advantageous in allowing particles to be more easily seen, even in fluid samples of high pigmentation or samples including debris.

The accumulated particles can then be analysed using a viewing means, (such as a microscope, image sensor, or other appropriate means) from above or below, or from both above and below. The image of the particles may be recorded and stored for reference or auditing purposes at a later time.

FIGS. 4 to 9 show another form of apparatus of the invention. The apparatus comprises a sample holder in the form of a vessel or flotation chamber 1 comprising a base 2 having an upper surface 2a and a lower surface 2b, and further comprising a projection 3 extending from the upper surface of the base 2.

A cylindrical wall 4 is joined to and extends from the base 2 at a distance from the projection so as to surround the projection and so that the upper surface 2a of the base and inner surface 4a of the wall form an internal fluid cavity or fluid well 5 in the vessel.

It will be appreciated that, although the drawings illustrate a cylindrical cavity wall joined to and extending from the base to form a cylindrical fluid cavity, it is envisaged that the cavity walls could, alternatively, be formed in other geometric shapes. For example, the cavity walls could be shaped to form a square or rectangular box section to form a fluid cavity having a cuboid or rectangular cuboid shape. Alternatively, the configuration of the cavity walls and base could form a fluid cavity having a pyramidal, hemispherical, or frustoconical shape. In such embodiments, the cavity walls have multiple interior surfaces because of the multiple walls forming the geometric shape.

Preferably, the surrounding wall(s) of the fluid cavity is/are equidistant from the projection so that the projection is located substantially at the centre of the fluid cavity. However, it is envisaged that, in some embodiments of the apparatus of the invention, the projection may be located off-centre relative to the wall(s) of the fluid cavity.

Figure 4:
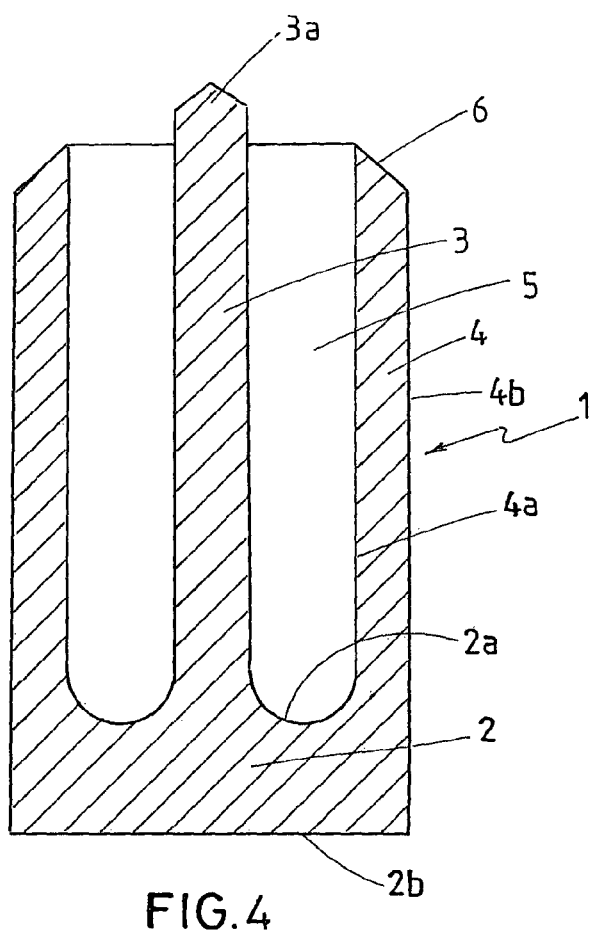
FIG. 4 shows a cross-sectional view through the centre of another embodiment of the invention.
Figure 6:
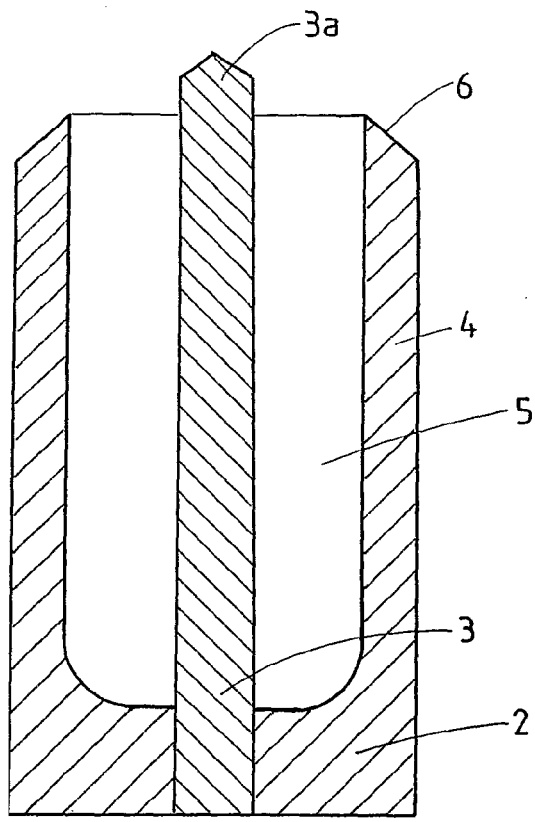
FIG. 6 shows a cross-sectional view through the centre of another embodiment of the invention.
Figure 7:
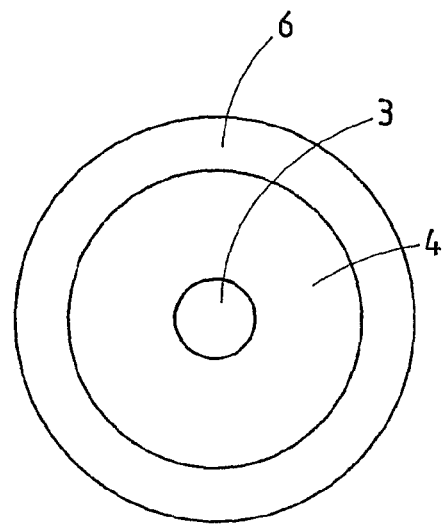
FIG. 7 shows a plan view of the embodiment shown in FIG. 6.
Figure 8:
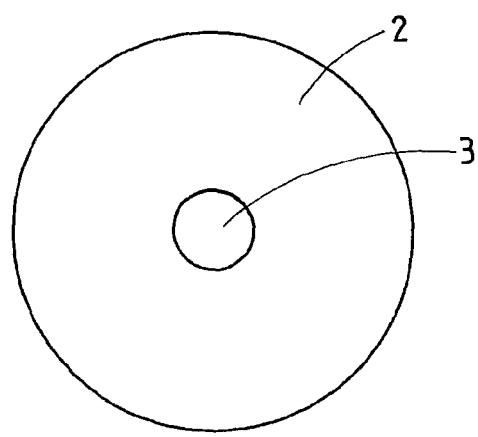
FIG. 8 shows a bottom view of the embodiment shown in FIGS. 6 and 7.

The upper surface of the fluid cavity base may be substantially flat, as shown in FIG. 6. Alternatively, the upper surface of the fluid cavity base may comprise a concave region surrounding the projection, as shown in FIG. 4, to ensure that the fluid cavity does not occlude or trap air bubbles when being filled with a fluid sample. In a preferred form, the base of the fluid cavity has a substantially hemispherical concave geometry, as shown in FIGS. 14a to 14f. Alternatively, the base of the fluid cavity may be convex or of any other suitable form.

In one form, the fluid cavity may be adapted to hold a certain volume of fluid to allow analysis of a fixed or known volume of fluid. For example, the fluid cavity may be dimensioned to hold a volume of fluid less than 10 ml; less that 1 ml; less than 100 µl; less than 10 µl; or less than 1 µl.

Preferably, the depth of the fluid cavity is less than 50 mm; less than 20 mm; less than 10 mm; or less than 1 mm.

Preferably, the diameter of the fluid cavity is less than 20 mm, less than 10 mm, or less than 1 mm.

Liquid menisci are created when cohesive interactions between the atomic or molecular particles of a liquid generate surface tension at the phase boundary of a fluid-liquid interface. The interface is caused to curve due to the interaction of the liquid with the surface of the container or at least one solid object. The curvature of a liquid meniscus can be either concave or convex.

Convex liquid curvature occurs when the atomic or molecular particles of the liquid have a stronger attraction to each other than to the interacting solid surface, or when liquids become pinned by sharp-edges. Contact angle hysteresis creates a convex meniscus due to the presence of edge energy sufficient to resist the progress of the liquid-solid contact line.

Concave liquid curvature occurs when the atomic or molecular particles of the liquid attract those of the container or another solid object.

As described above, the projection of the apparatus of the invention comprises a substantially fluid wettable contact region or surface that exhibits properties that allow the contact region to be substantially wetted by a fluid sample, when the apparatus is in use, so that the fluid sample forms a meniscus having its apex in contact with the projection. Preferably, the contact region is located at the distal end of the projection and may or may not include the tip of the projection.

Thus, by changing the surface texture or by changing the chemical nature of the surface of at least the contact region of the projection and/or the base and/or the cavity wall(s) in the apparatus of the invention, it is possible to change the profile of the fluid meniscus that is formed when the apparatus is in use.

Thus, the base and/or wall(s) of the fluid cavity may be formed of a material, or coated with a material, that renders the base and/or wall(s) either: hydrophobic; super-hydrophobic; oleophobic; fluorophobic; ionic; cationic; anionic; or to have specific physicochemical properties. The base and/or wall(s) of the fluid cavity may be fabricated from, or coated with, any type of material that substantially controls wetting of the surface by repelling fluid to facilitate the formation of a fluid meniscus having its apex either in contact with the fluid wettable contact region of the projection when the fluid cavity is filled with fluid, or having its apex above the end of the projection and positioned substantially centrally between the wall(s) of the fluid cavity. For example, the base and/or cavity wall(s) could be formed from, or coated with, polymers; polypropylene; polyester; nylon; olefins; cyclic olefin copolymer; poly tetrafluoroethylene (PTFE, Teflon®), acrylic; polycrystalline solids; glass; quartz; a composite material that comprises a combination of two or more of these materials; or any other material that facilitates the formation of a fluid meniscus having a desired profile when fluid is held within the fluid cavity. Alternatively or additionally, the base and/or cavity wall(s) may be coated with chemicals; silanes; or silicones to facilitate a desired fluid meniscus when the apparatus is in use.

At least the contact region of the projection may be formed from, or coated with a material that renders it hydrophilic, super-hydrophilic, oleophilic or fluorophilic. In particular, the contact region of the projection may be coated with particles such as silicon dioxide, titanium dioxide or doped titanium dioxide so as to render it hydrophilic or super-hydrophilic.

Similarly, at least the contact region of the projection and/or the base and/or the cavity wall(s) may have a textured surface to facilitate the formation of a fluid meniscus having a desired profile when the apparatus is in use. That is, the base and/or wall(s) of the fluid cavity may be textured so as to render the surface hydrophobic or super-hydrophobic and at least the contact region of the projection may have a textured surface so as to render it hydrophilic or super-hydrophilic. For example, the base and/or cavity wall(s) may be textured by smoothing its/their surface to facilitate a desired fluid meniscus when the apparatus is in use. Conversely, at least the contact region of the projection, or substantially the entire projection, may be textured by roughening its surface to facilitate a desired fluid meniscus when the apparatus is in use.

The base of the fluid cavity or vessel is preferably formed from, or coated with, the same material as that of the cavity wall(s), especially where the base and wall(s) are integrally formed as one part, as shown in FIG. 4. However, it is envisaged that the base and cavity wall(s) could be formed from, or coated with, different materials, especially if the base and wall(s) are formed as separate parts that are then joined together to form the vessel, as shown in FIG. 4.

Returning to FIGS. 4 to 8, the free end of the cavity wall 4 farthest from the base 2 terminates in an edge 6 that defines an opening to the fluid cavity 5. However, it is envisaged that the opening to the fluid cavity may be provided by any other suitable configuration as would be readily apparent to a person skilled in the art.

Figure 5:
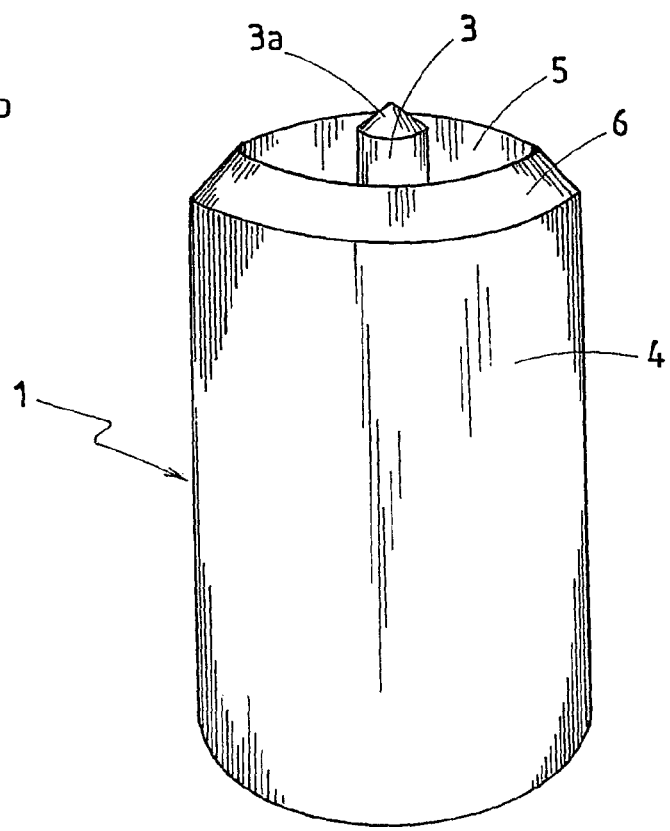
FIG. 5 shows a perspective view of the embodiment shown in FIG. 4.

In one form of the invention, as best seen in FIGS. 4 to 6, the cavity wall is thick to provide a thick edge 6, which is chamfered to form an outwardly sloping surface in the direction of the base 2. That is, the edge 6 is sloped so that the free end of the interior surface of the cavity wall 4a is distanced farther from the base than the free end of the exterior surface of the cavity wall 4b.

With this arrangement, when the apparatus is in use and fluid is added to the fluid cavity 5, the chamfered edge 6 of the wall 4 encourages any excess fluid to be dispelled or shed from the fluid cavity 5, thus enabling the vessel 1 to be consistently filled without a metering instrument. In the form of the invention shown, the diameter of the fluid cavity is 8 mm and the cavity wall is 2 mm thick, although it will be appreciated that the fluid cavity and cavity wall could be of any suitable diameter and thickness respectively.

It is envisaged that the edge of the cavity wall(s) may, alternatively, take many forms without departing from the scope of the invention, as would be readily apparent to a person skilled in the art. For example, the cavity wall(s) may be substantially thin with a sharp edge or the edge of the cavity wall(s) may be substantially blunt, being a squared edge or a curved edge.

Returning now to the projection 3 that extends from the base 2 of the apparatus, as shown in FIGS. 2 to 6 and FIG. 9. The distal end 3a of the projection is tapered toward the tip of the projection so that the tapered portion of the distal end forms a conical tip with downwardly sloping sides.

Figure 10:
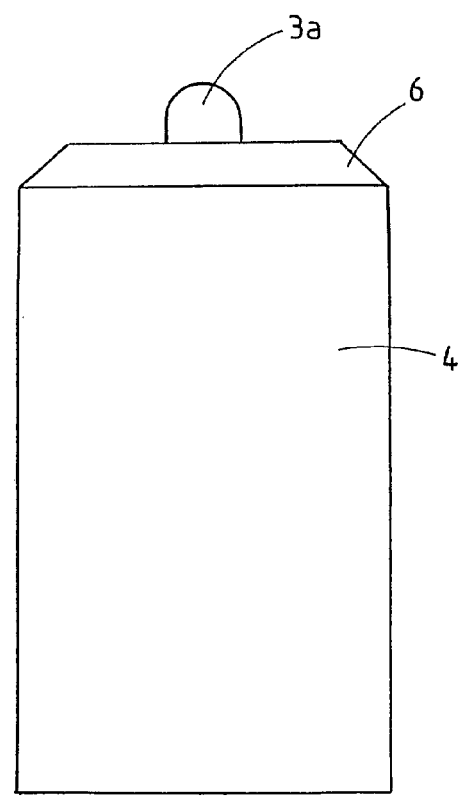
FIG. 10 shows a side view of another embodiment of the invention.
Figure 14B:
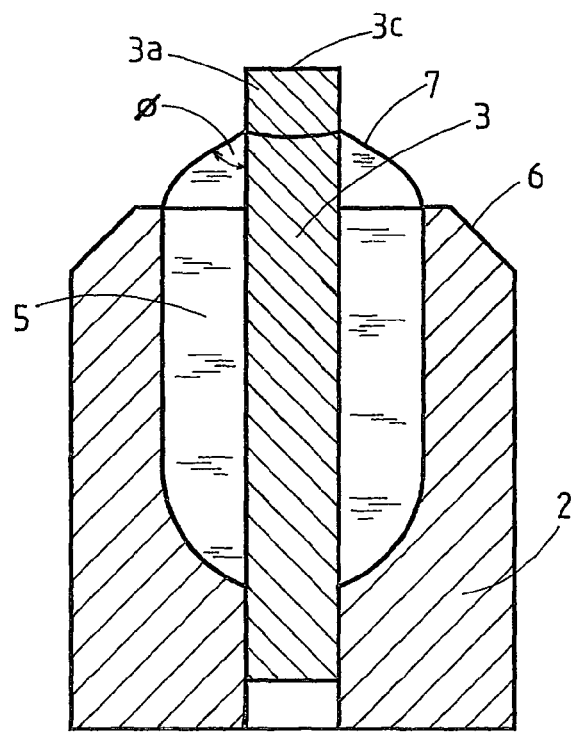
Figure 14C:
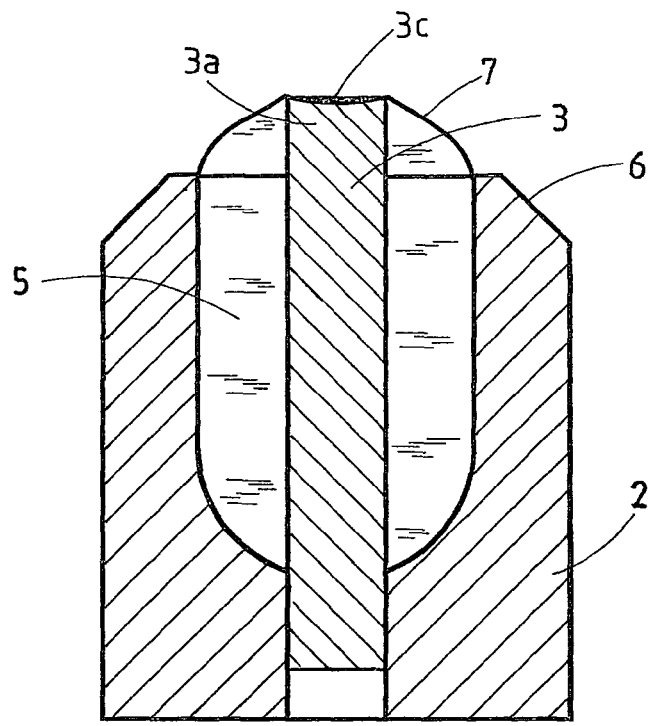
Figure 14D:
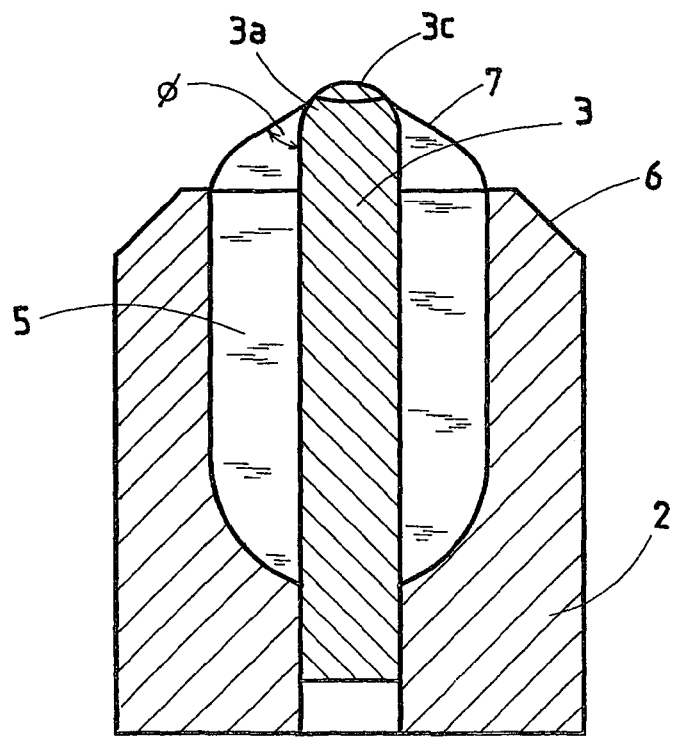
Figure 14E:
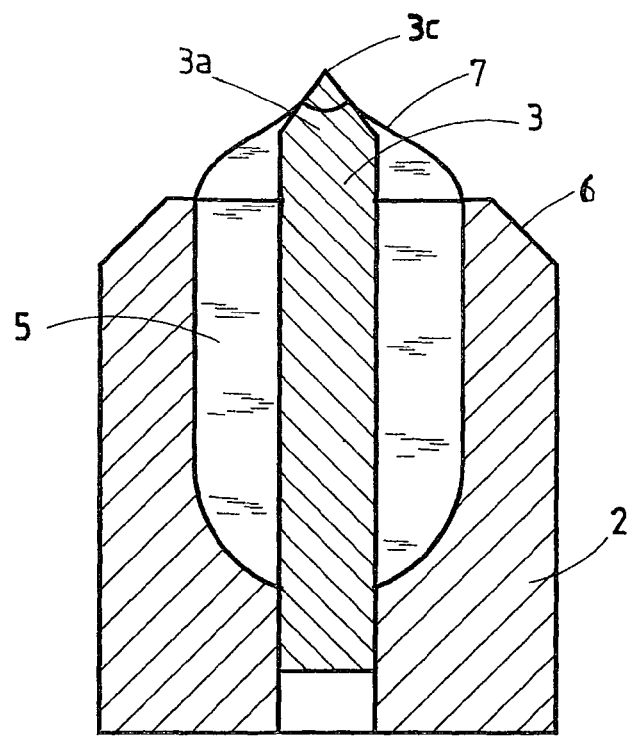
Figure 14F:
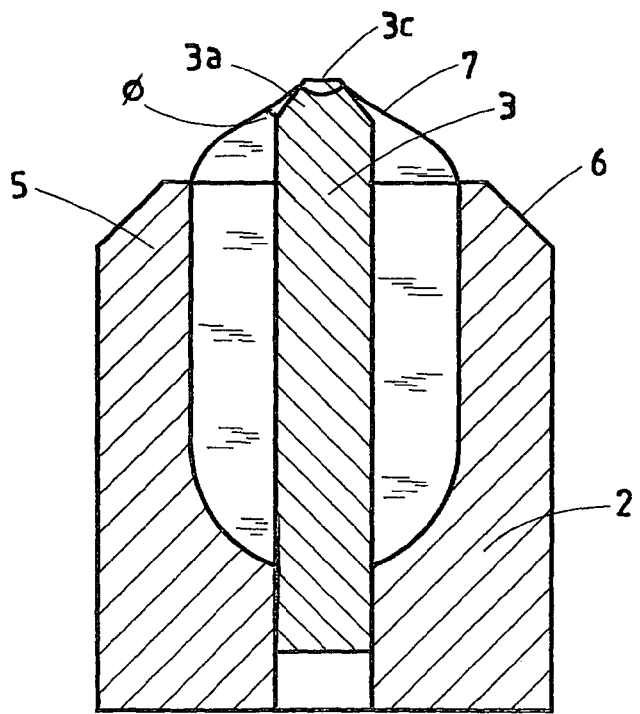

However, the distal end 3a of the projection is not limited to this embodiment and may, instead, take many different forms. For example, the tapered distal end 3a of the projection may be of a convex, substantially curved hemispherical shape as shown in FIG. 10 and FIG. 14d. Alternatively, the distal end 3a of the projection may have a substantially flat tip 3c, as shown in FIGS. 14a to 14c. In another alternative embodiment, the tapered distal end 3a of the projection may be substantially frustoconical, as shown in FIG. 14f. In other alternative embodiments, the distal end 3a of the projection may be graduated; stepped; or chamfered to form a pyramidal shape. Alternatively, the entire projection, or substantially the entire projection, may be tapered toward its tip.

In preferred embodiments, the distal end of the projection may be shaped, dimensioned, and positioned relative to the edge of the cavity wall(s) so that, in use, at least a portion of the distal end of the projection allows for a region of reduced fluid depth in the fluid sample, the fluid depth in this region being the distance between the surface of the fluid and the distal end of the projection. In preferred forms of the apparatus of the invention, the depth of fluid between the apex of the fluid meniscus and at least one portion of the fluid wettable projection is less than 10 mm; less than 5 mm; less that 2 mm; less than 1 mm; less that 100 µm; or less that 10 µm. Alternatively, at least one portion of the distal end of the projection extends beyond the surface of the fluid meniscus by a distance that is less than 10 mm; less than 5 mm; less that 2 mm; less than 1 mm; less than 100 µm; or less that 10 µm.

As shown in FIGS. 4 to 9, it is preferred that at least a portion of the distal end 3a of the projection extends 3 beyond the free end or edge 6 of the cavity wall 4. However, it is envisaged that the tip of the projection may, alternatively, terminate within the fluid cavity so that the height of the cavity wall(s) is greater than that of the projection.

The apparatus may be adapted to allow the projection to move relative to the base so that the distal end of the projection may be moved closer to, or farther from, the base. This also allows the tip of the distal end of the projection to extend above or below the edge of the fluid cavity wall(s).

As described above, the apparatus may optionally include at least one illuminating means to allow a user to more easily view particles in at least the region of fluid immediately surrounding the contact region or distal end of the projection by illuminating this region when the apparatus is in use. The at least one illuminating means may be selected from the group comprising, but not limited to: lights; lamps; bulbs; lasers; light emitting diodes (LEDs); laser diodes; cameras; fibre optic cables; lenses; microscopes; or any other suitable component.

In one form, the projection and/or the base of the fluid cavity may be adapted to illuminate at least a portion of the fluid sample when the apparatus is in use. For example, the projection may comprise a rod 3 having a base portion for attachment to the base 2 of the vessel 1, a central body portion, and a distal end 3a. The distal end of the rod defines the contact region. Preferably, at least the contact region of the distal end of the rod is formed of substantially transparent or translucent material. Alternatively, the whole of the distal end or the rod or only the tip of the rod may be substantially transparent or translucent. In one preferred form, the entire rod is formed from such light transmitting material so as to be substantially transparent or translucent. The rod provides a conduit through which a light source can transmit or project light to illuminate at least a portion of the area surrounding and including the contact region at the distal end of the rod, especially the region or fluid where the fluid meniscus contacts the rod or where the fluid surface sits above the rod when the apparatus is in use.

The light source may be housed within the rod or within the base of the vessel. Alternatively, the light source may be located external to the vessel and connected to the rod to allow light to be transmitted from the light source to the distal end of the rod or to a point near the distal end of the rod.

As mentioned above, substantially the whole rod, or only its distal end, may be fabricated of any light transmitting solid material, such as, but not limited to: polymers; acrylic; polycrystalline solids; and glass, especially borosilicate glass.

It is envisaged that the light transmitting projection need not take the form of a rod, but could comprise any other suitable form that allows light to be transmitted through the projection to illuminate at least the region immediately surrounding the distal end of the projection, as would be readily appreciated by a person skilled in the art.

Alternatively, or additionally, and as described above, the apparatus of the invention may include at least one viewing means to allow a user to view particles in the region of the fluid sample that at least immediately surrounds the contact region or distal end of the projection or that lies above the distal end of the projection. The viewing means may be positioned above, below, or at the side of the apparatus. Similarly, images of the apparatus and fluid sample captured by the viewing means may be taken from above, below, or from the side of the apparatus.

The viewing means operates by transmitting at least one image of the region to a display device or to an image storage device where the image can be recorded and stored for viewing at a later time.

The at least one viewing means may be selected from one or more of the group comprising, but not limited to: cameras; microscopes; digital image sensors, such as charge coupled device (CCD) sensors or complementary metal oxide semiconductor (CMOS) sensors for example; analogue image sensors; computer screens; personal digital assistants (PDAs) having a display screen; telephones, including mobile telephones and radiotelephones having a display screen; and other suitable image display devices.

Figure 9:
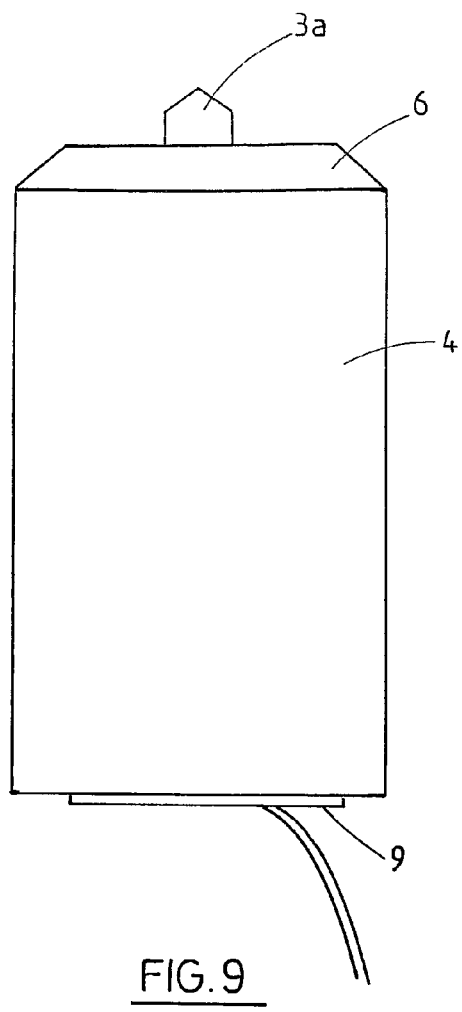
FIG. 9 shows a side view of the embodiment shown in FIGS. 6 to 8 in which a portion of one form of viewing means can be seen.

In one form of apparatus of the invention, as shown in FIG. 9, the projection comprises a plurality of optical fibres fused together to form the projection. The projection provides a conduit along which images can be transmitted from the distal end of the projection to image the region of the fluid sample immediately surrounding the distal end of the projection when the apparatus is in use. The plurality of optical fibres that form the projection are coupled to a viewing means 9 comprising an image sensor.

The image sensor is located at the base of the projection to monitor the region surrounding and including the distal end of the projection. The image sensor is also coupled to an image storage device and/or display device that displays the image captured by the image sensor to allow a user to view the image to detect and/or identify and/or count particles.

In a preferred form, the image sensor comprises a CCD or CMOS image sensor that captures the image of the fluid sample in at least the region immediately surrounding the contact region or distal end of the projection when the apparatus is in use.

Again, to help provide a clear image of any particles above the distal end of the projection, or of particles surrounding the contact region of the projection, the fluid sample may be illuminated from above or from the side by illuminating means, such as a light source integral with the apparatus or an external light source. Alternatively, the fluid sample may be illuminated from below or the side by light emitted from the projection, or from below by might emitted from the base of the fluid cavity. Where light is emitted from the base of the fluid cavity, the base comprises a light transmitting region, which may be transparent or translucent, through which light is projected. The captured image can then be transmitted to an image storage or display device to store or display the recorded image for subsequent examination, such as for the detection and/or identification and/or counting of particles.

The storage or display device may be selected from the group comprising, but not limited to: visual display units; computers; liquid crystal displays; plasma displays; cathode ray tubes; printers; personal digital assistants (PDAs); computer networks, including the internet; telephones, including mobile telephones and radiotelephones; transmitters; transceivers; global positioning system (GPS) enabled devices; and other suitable image recording and/or display devices.

Figure 13:
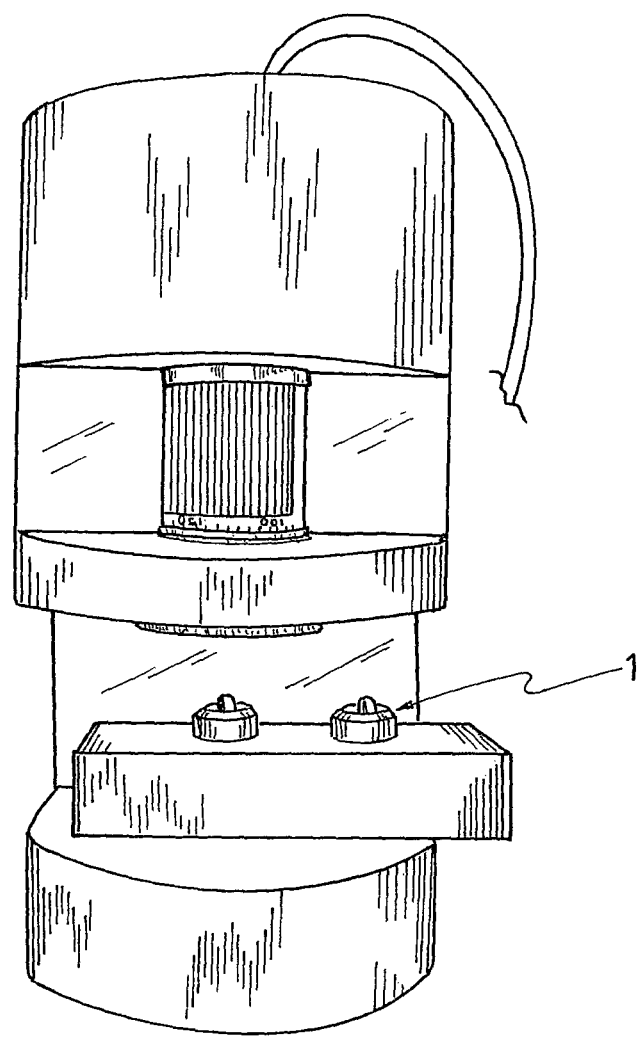
FIG. 13 shows a perspective view of another embodiment of the invention when viewed under a microscope.

Thus, the apparatus of the invention may include, or may be used with (as shown in FIG. 13), a viewing means that optionally allows a permanent record of the image to be easily created.

In another form of apparatus of the invention, the viewing means comprises a microscope, lens, or other image magnifying device. The viewing means may form part of the apparatus of the invention or the viewing means may be an external device that is used together with the apparatus of the invention to view any particles within the fluid sample tested using the apparatus of the invention.

In a preferred form of the invention, the contact region of the projection, or the distal end of the projection, and at least a portion of the fluid cavity surrounding the projection are dimensioned to correspond to at least one microscopic field of view at an appropriate magnification when viewed using an upper viewing apparatus positioned above the device, a lower viewing apparatus positioned below the device (such as a CCD or CMOS image sensor for example), or a combination of upper and lower viewing apparatuses. When this region to be analysed corresponds to a single microscopic field of view, translation of a microscope is not necessary to see particles within the region.

The projection used in the apparatus of the invention preferably has a diameter or width of less than 10 mm, less than 5 mm, less than 1 mm, less than 0.5 mm, or less than 0.1 mm.

The method of analysing particles using this form of apparatus of the invention will now be described.

Prior to use of the apparatus, at least the contact surface of the projection, or substantially the whole projection, may be wiped with detergents or surfactants (such as cationic surfactants, anionic surfactants, or zwitterionic surfactants) to make the targeted surface hydrophilic or super-hydrophilic to produce the desired meniscus in the type of fluid sample to be used. If a surface of the projection is coated with titanium dioxide or doped titanium dioxide, the projection may need to be exposed to UV light to render it hydrophilic or superhydrophilic.

The apparatus is then positioned so that the base of the fluid cavity is substantially horizontal.

The fluid cavity 5 of the apparatus is loaded with an unmetered volume of a fluid sample so that the surface of the fluid sample lies below the tip of the projection. The design of the fluid cavity ensures that a fixed volume of fluid is retained within the fluid cavity. In particular, the chamfered edge 6 of the cavity wall(s) 4 causes excess fluid to be shed from the fluid cavity to limit the maximum volume of fluid that can occupy the fluid cavity. Because the chamfered edge 6 limits the maximum volume of fluid that can be held within the fluid cavity 5, the fluid cavity can be loaded with an unmetered volume of fluid.

The substantially wettable contact region of the projection 3 is now wetted by the fluid. The wetted contact region causes the meniscus to be curved to form an apex where the meniscus contacts the projection, as shown in FIGS. 11 and 14d to 14f.

The fluid is of such a depth that the apex of the meniscus contacts the contact region at the distal end of the projection.

The contact angle between the surface of the fluid and the edge of the fluid cavity is preferably greater than 30°, greater than 60°, greater than 90°, or greater than 120°.

It is envisaged that the apparatus and method may be adapted to create a different shaped meniscus, if desired. The shape of the meniscus can be determined based on selected properties of the fluid cavity wall and/or base and/or properties of the projection and/or properties of the fluid. Such properties of the fluid cavity and projection are selected from the group comprising, but not limited to: the geometry; shape; position; orientation; configuration; physical texture; chemical texture; hydrophobicity; and hydrophilicity. Such properties of the fluid are selected from the group comprising, but not limited to: buoyancy; density; mass; specific gravity; miscibility; surface tension; contact angle; surface energy; charge; electrostatic charge; electrostatic surface charge; dipole moment; polarity; temperature; and concentration.

The sample is then left for a period of time (for example, 1 minute to 5 minutes or longer) to enable buoyant particles to ascend within the fluid and migrate toward the apex of the meniscus. The particles converge at the region surrounding and including the apex of the fluid meniscus at the contact region of the projection. This region of particle accumulation preferably corresponds to a single microscopic field of view.

The particles that accumulate at the apex region of the fluid meniscus, and that directly touch the projection, become substantially immobilised due to the adhesive forces between the particles and the projection. Other particles that do not directly touch the projection also become substantially immobilised with other particles touching the projection or other substantially immobilised particles.

Figure 12:
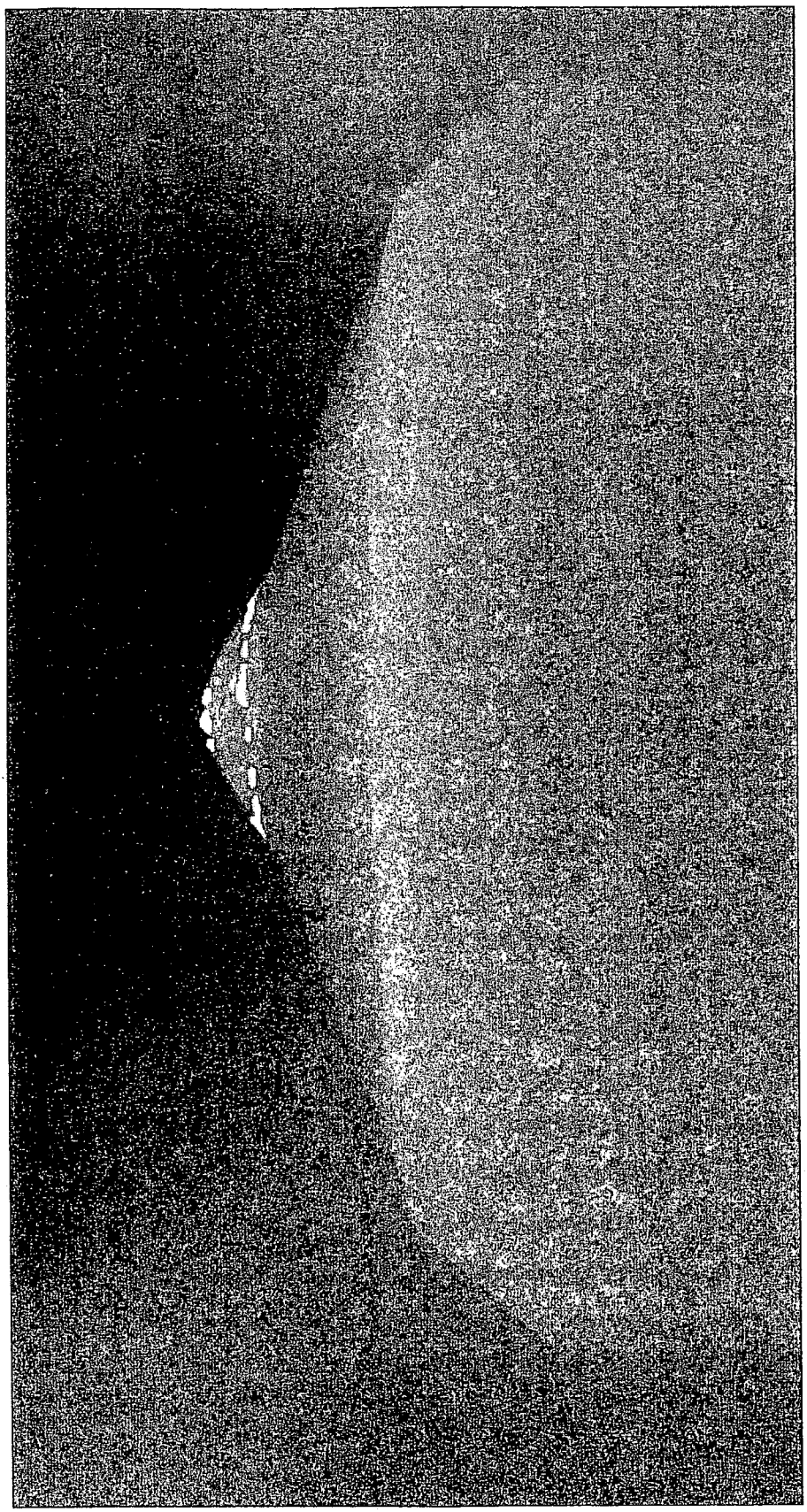
FIG. 12 shows the embodiment of FIG. 11 in which the particles at the apex of the meniscus of the fluid sample are illuminated.

The fluid sample and any particles present may optionally be illuminated by a light source directing light onto the sample from above or from the side. Alternatively, the apparatus may be adapted to illuminate at least a portion of the sample by transmitting light from the base of the apparatus along the projection, or by transmitting light through the distal end of the projection or through substantially its whole body. FIG. 12 shows particles that have been illuminated by light emitted from the distal end of the projection.

The particles can then be analysed by viewing the accumulated particles from above using a viewing means, such as a microscope or an image sensor, or viewed from below using a viewing means such as an microscope or an image sensor, or from both above and below. The presence of the particles can be detected, the types of particles can be identified, and the number of particles can be counted.

In another embodiment, as shown in FIG. 13, the apparatus of the invention comprises multiple sample holders 1 or vessels mounted on a base plate. The base plate may take the form of microtitre trays.

In another form, the apparatus of the invention may comprise a disposable or reusable cassette comprising a vessel having at least one fluid cavity (as described above) from which extends a projection having a fluid wettable contact region as described above. Again, the apparatus may include illuminating means and the apparatus can be used in conjunction with a viewing device that may form part of the apparatus or that may be separate from the apparatus, as described above.

In each embodiment of the invention, it is preferred, but not essential, that at least the diameter or width of the contact region or distal end of the projection and the width of the meniscus surrounding the projection are dimensioned to correspond to a single microscopic field of view. Alternatively, the whole of the fluid cavity, including the projection and particles within the fluid cavity, may optionally correspond to a single microscopic field of view. Whether or not the area to be examined falls within a single microscopic field of view depends on the size of the projection, or the size of the microscope, or the magnification required, or the size of the particles. Therefore, in other aspects of the invention, multiple fields of view may be necessary to analyse particles.

Whether or not the area to be examined corresponds to a single microscopic field of view depends on the properties of the wall(s) and/or base of the fluid cavity and/or properties of the projection and/or properties of the fluid and/or properties of the particles. Examples of properties of the wall or base of the fluid cavity or projection are: dimensions; geometry; shape; position; orientation; configuration; texture; physical texture; chemical texture; hydrophobicity; and hydrophilicity. Examples of properties of the particles are: buoyancy; density; charge; electrostatic charge; electrostatic surface charge; mass; size; and specific gravity. Examples of properties of the fluid are: miscibility; surface tension; contact angle; surface energy; charge; electrostatic charge; electrostatic surface charge; dipole moment; polarity; pH; temperature, and concentration. The size of the microscope and the magnification required will also affect whether or not the desired area for analysis corresponds to a single microscopic field of view. Therefore, in some aspects of the invention, it is envisaged that multiple fields of view may be necessary to analyse particles using the apparatus and method of the invention.

Where the apparatus is adapted to encourage the particles to accumulate within a single microscopic field of view, the presence of particles, type of particles, and number of particles can be counted without needing to translate the microscope (when a microscope is used during the analysis). The image viewed through the microscope can be projected onto a display screen, such as a computer screen for example, for ease of analysis. The image can also be recorded and electronically communicated or stored for later reference or for auditing.

Alternatively, where the apparatus of the invention comprises a CCD or CMOS image sensor coupled to fibre optic cables within the projection, the image sensor can transmit the image, captured through the distal end of the projection, to a display screen for analysis. Again, the image can be recorded and stored for later reference or for auditing.

Figure 11:
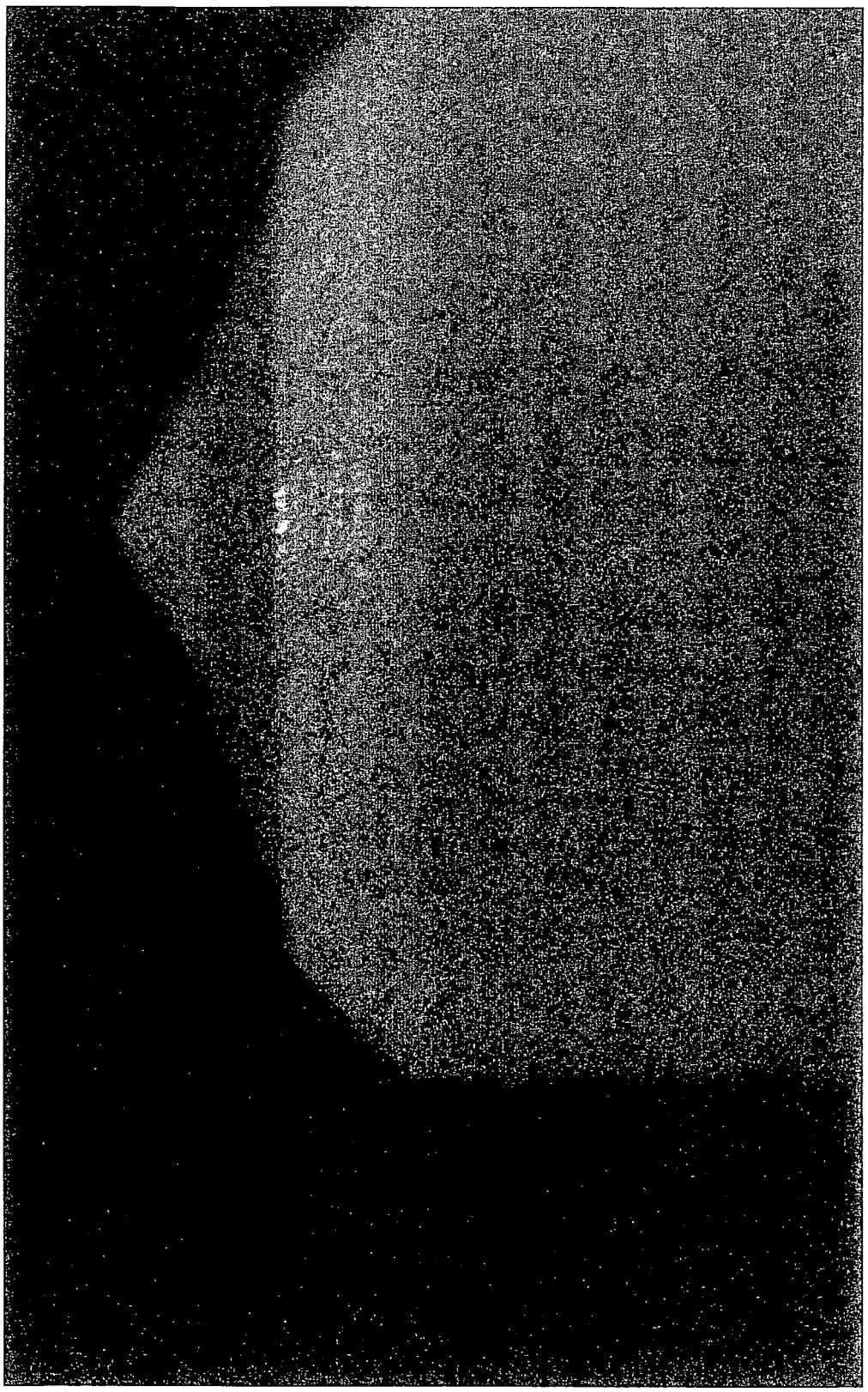
FIG. 11 shows the embodiment of FIGS. 6 to 9 in use so that the meniscus of the fluid sample can clearly be seen between the walls of the fluid cavity and the tip of the projection.

In another embodiment, as shown in FIGS. 10 to 12, the apparatus of the invention provides a sample holder in the form of a vessel comprising a fluid cavity wherein both the cavity wall(s) and base are fabricated from PTFE, the vessel also comprises a projection fabricated from borosilicate glass. The projection has a tapered distal end having a conical or rounded tip that extends above the upper edge of the cavity wall(s). The contact region is located at the distal end of the projection and excludes the tip of the projection. The glass projection provides a light transmitting conduit to transmit light from a light source through the transparent distal end of the projection.

When the cavity is filled with a volume of fluid, the fluid forms a meniscus having its peak or apex in contact with the contact region at the tapered distal end of the projection. This arrangement provides a path for buoyant particles to ascend and converge at the apex of the meniscus and at the region proximate to the tip of the projection. The tapered distal end of the projection allows for a reduced fluid depth in this region. The fluid depth between the surface of the fluid and the tapered end of the projection is shallowest at the apex of the meniscus and gradually increases. The reduced fluid depth allows particles that accumulate in the region of reduced fluid depth to come into contact with the tapered surfaces of the projection, at which point the particles cease to move freely within the fluid and they instead become substantially immobilised due to the adhesive forces between the projection and the particles.

Figure 15:
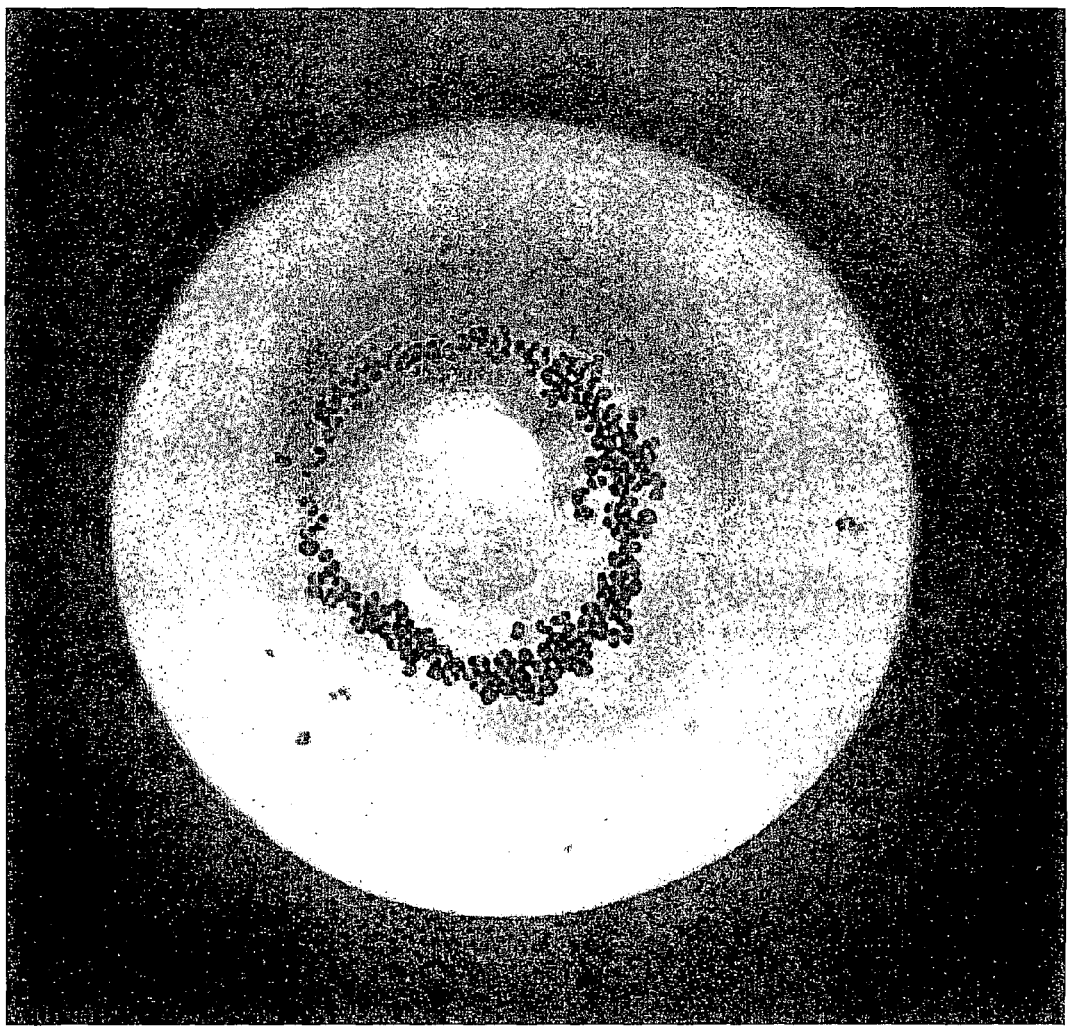
FIG. 15 shows a digital image of the apparatus of the invention when used to analyse a fluid sample containing pollen particles.

Smaller particles tend to accumulate closest to the contact line where the apex of the fluid meniscus contacts the projection. The smaller diameter of such particles allows the particles to beach in the shallower fluid where the distance between the surface of the meniscus and projection (the depth) is the least. Larger particles tend to accumulate further away at the point at which they contact the projection. The larger diameter of these particles means that they are caused to beach in deeper fluid than the smaller particles. Where the sample includes many particles, the particles tend to accumulate around the projection to form an annular ring, as shown in FIG. 15.

The apparatus of the invention may be vibrated to encourage the particles to separate themselves by size, the smaller particles accumulating closest to the tapered distal end of the projection where the fluid depth is shallowest.

Light emitted from the projection illuminates the fluid sample and particles in the region proximate to the contact region of the projection, as shown in FIG. 12.

The fluid sample and any particles present can then be analysed using a viewing device, such as a microscope, or image sensor, or both, as described above. Similarly, the image can be recorded and electronically transmitted or stored for later reference or for auditing. Preferably, the accumulated particles lie in at least one single image frame to allow the image to be captured without translation of the viewing device.

In another embodiment of the invention, the apparatus comprises a sample holder comprising a fluid cavity defined by a base and a cylindrical wall with a chamfered upper edge that defines an opening to the fluid cavity. The sample holder further comprises a projection in the form of a solid glass cylindrical rod with a hemispherical distal end. The rod is centrally located in the fluid cavity.

When the cavity is loaded with fluid, the fluid forms a meniscus with a radius of curvature that may depend on the diameter of the opening of the fluid cavity and may also depend on the contact angle between the fluid and the chamfered edge of the fluid cavity wall(s). The base of the cavity has a substantially hemispherical geometry to ensure that the cavity does not occlude or trap air bubbles when being filled with fluid and to ensure that the volume of fluid retained in the fluid cavity is substantially constant from sample to sample.

The depth and diameter of the fluid cavity and the radius of curvature of the meniscus determines the total volume of the sample to be analysed. The circular cross-sectional geometry of the cavity ensures that when the base of the apparatus is horizontal during use, the apex of the fluid meniscus is located along the central longitudinal axis of the fluid cavity.

The glass rod has a contact region located at its hemispherical distal end that extends through the surface of the fluid sample and protrudes 0.2 mm above the surface of the apex region of the fluid meniscus, as shown in FIG. 14d. Particles within the fluid are caused to accumulate at the apex of the meniscus, which is in contact with the hemispherical end of the projecting rod, preferably within a single microscopic field of view. The particles can be analysed from above by a microscope or alternative form of viewing means, as shown in FIG. 14.

In one form of apparatus and method of the invention, as shown in FIG. 14a, the apparatus and method are adapted so that the distal end of the projection lies below the surface of the fluid sample when the apparatus is in use. The projection is formed from a cylindrical glass rod that extends through a fluid cavity formed from PTFE. The rod terminates beneath the surface of the apex region of the liquid meniscus. The end of the rod acts as a floor to limit the depth of liquid beneath the apex region of the liquid meniscus. The rod also provides a conduit for light to be projected along the axis of the glass rod to illuminate at least the portion of the fluid sample above the rod for illumination of the apex region of the liquid meniscus for optical microscopy. Alternatively, the rod may be formed from a plurality of fibre optic cables fused together and coupled to an image sensor, such as a CCD or CMOS sensor.

In use, at least a portion of the fluid sample is illuminated by the rod and an image of at least the area of fluid immediately surrounding the distal end of the rod is captured and recorded. The image is optionally electronically transmitted to a storage device to create a permanent record for later reference or for auditing. In this form, it is not essential for the projection of the apparatus to possess any particular properties to affect the profile of the fluid meniscus when the apparatus is in use, because the fluid meniscus will form above the projection Thus, the apparatus and method allow for better visibility of particles, by encouraging particles to accumulate in one region, by reducing the depth of fluid in this region, and by illuminating this region of fluid from below. Additionally, or alternatively, the region may be illuminated from above or from the side.

The ability of the apparatus and method of the invention to create a region in which particles accumulate, in which the depth of fluid is reduced, and in which the region is illuminated, makes it significantly easier for particles to be detected, identified, and counted when held in a fluid sample containing debris and pigmentation.

EXAMPLE 1

The apparatus and method of the present invention was compared with the McMaster approach to particle analysis. A McMaster-type slide was acquired for the analysis of 0.5 ml fluid samples of pollen grains in a stock sample of pollen extracted from a male Picea cone.

The apparatus included a sample holder in the form of a fluid cavity fabricated from a 25 mm length of 12 mm diameter PTFE rod. The fluid cavity had an 8 mm diameter and the free edge of the fluid cavity was chamfered to slope outwardly and downwardly at 45°. A projection was formed from a 20 mm length of 3 mm diameter borosilicate glass rod. The entire projection, including the contact region, was superhydrophilic so as to be substantially fluid wettable for the type of fluid sample being used.

The glass rod comprised a conical tip at its distal end with an open angle of 120°. The opposing bottom end of the glass rod was a polished flat surface. The glass rod was positioned within a centrally located aperture in the base of the fluid cavity, and was located so that the apex of its conical tip projected approximately 1.3 mm above the edge, of the fluid cavity.

The pollen particles were suspended in a 15 ml volume of saturated NaCl solution and different dilutions were prepared using additional saturated NaCl solution as the diluent.

In the analysis, samples of the diluted stock solution were thoroughly mixed by rapid inversion seven times followed by extraction of an aliquot for analysis.

For the McMaster method, a plastic bulb pipette was used to load the slide, which was then carefully transferred to an optical microscope.

The apparatus of the present invention was filled with a 0.5 ml aliquot using a P1000 Gilson pipette. The apparatus was then positioned in an optical microscope fitted with a digital camera and the image was presented on a visual display unit.

After waiting 2 minutes for the particles to equilibrate, the particles in the McMaster-type slide were manually counted during systematic x-y translation of the slide.

Particles that accumulated at the apex of the meniscus surrounding the contact region of the glass rod of the present invention were manually counted on the visual display unit and electronically captured and stored.

Picea pollen grains accumulated at the apex of the meniscus surrounding the distal end of the glass rod. Thus, the grains accumulated in an annular configuration on or near the surface of the conical distal end of the glass rod.

The depth of liquid from the fluid surface to the surface of the glass rod has a changing depth profile due to the curvature of the fluid meniscus and due to the tapered distal end of the glass rod. The pollen particles ascend until the depth of the fluid is approximately equal to the diameter of the particle and the interaction between particle and tapered surface of the distal end of the glass rod prevents the pollen particle from ascending any further.

FIG. 15 is a digital image showing the formation of a liquid meniscus and the accumulation of 142 pollen particles into a single field of view using the apparatus of the invention.

The glass rod and the region proximate to the contact region at the tapered distal end of the rod are illuminated by a white light emitting diode (LED).

In one example, the present invention was compared to the McMaster-type slide. Table 1 shows the results of pollen counting between the two methods. The results in this table show the difference in being able to accurately count pollen particles from aliquots of a $1\times10^{-3}$ dilution of the pollen stock solution using the McMaster method compared to the method of the present invention. The apparatus of the invention was filled with a 0.5 ml aliquot using a P1000 Gilson pipette.

With a sample size of 32 independent measurements of the same diluted sample, systematic differences between the two methods were evident, namely a difference in the total number of pollen particles counted and the degree of variability in the measurements as expressed by the standard deviation.

TABLE 1

| Measurement | McMaster Slide | Present Invention |
| --- | --- | --- |
| Average number of particles counted per 0.5 ml | 22.1 | 27.0 |
| Standard Deviation | 5.5 | 4.4 |

Overloading of the apparatus of the invention and inaccurate calibration of the McMaster-type slide volume were eliminated from being factors potentially contributing to the disparity in the counted pollen numbers. Additionally, pollen particles obscured by the printed grid lines of the McMaster-type slide, which are 178 microns wide and correspond, to 15.8% of the total volume, are accommodated for in the sample volume analysed. Thus, the results indicate that some other factor, potentially related to the loading of the sample and/or the geometry of the McMaster-type slide, has led to a systematic undercount of pollen particles, determined to be 18.5%.

EXAMPLE 2

In another example, the apparatus and method of the invention were used to determine the numbers of pollen particles in a prepared dilution series. In the analysis, dilutions of the pollen stock solution were thoroughly mixed by rapid inversion seven times followed by extraction of an aliquot for analysis. The apparatus of the invention was filled with a 0.5 ml aliquot using a P1000 Gilson pipette. The apparatus was then positioned in an optical microscope fitted with a digital camera and the image was presented on a visual display unit.

After waiting 2 minutes for the particles to equilibrate, particles accumulated at and near the apex of the meniscus surrounding the contact region at the distal end of the glass rod. The particles were counted manually on the visual display unit. Each measurement was repeated 6 times and the process was then repeated with a fresh dilution series to generate at least 12 measurements per dilution.

TABLE 2

| Dilution ($\times 10^{-4}$) | Sample size | Average count (per 0.5 ml) | Standard deviation |
| --- | --- | --- | --- |
| 1 | 12 | 3.9 | 2.6 |
| 2 | 12 | 6.4 | 2.8 |
| 4 | 12 | 12.3 | 3.8 |
| 6 | 12 | 18.2 | 3.9 |
| 8 | 12 | 22.0 | 5.0 |
| 10 | 48 | 26.8 | 4.3 |

Figure 16:
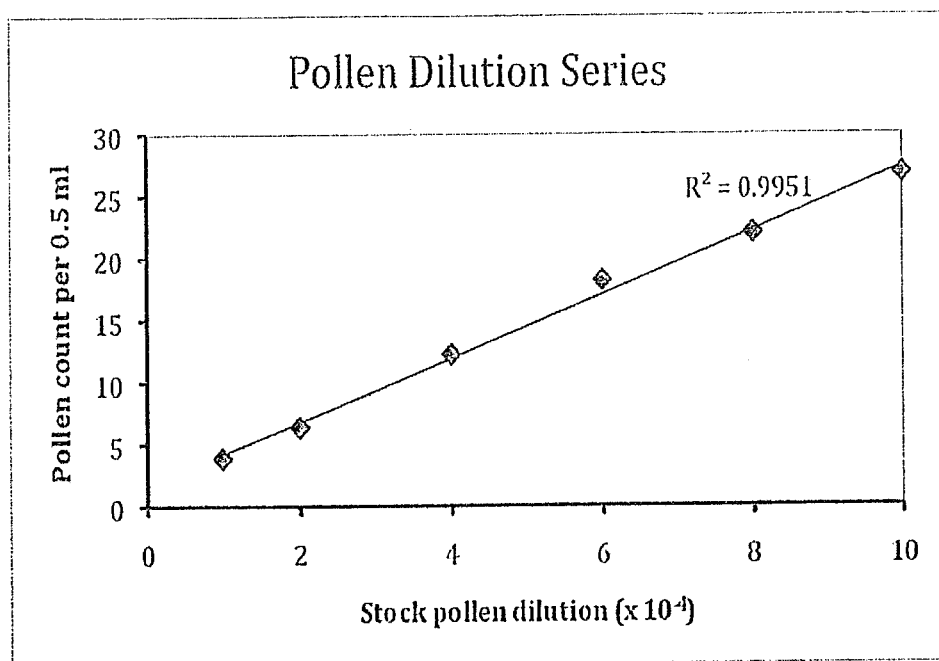
FIG. 16 shows a graph of data collected when using the apparatus of the invention to analyse a fluid sample containing pollen particles.

FIG. 16 shows a graph of the data of Table 2 displaying the pollen count per 0.5 ml aliquot versus the pollen dilution. The plotted points were fitted to a line ($R^2=0.995$ which is significant) and illustrates that the apparatus and method of the present invention enable systematic pollen counting and responds linearly to pollen concentration in the sample range tested.

EXAMPLE 3

The apparatus and method of the invention can also be used to analyse faecal material to detect and/or identify and/or count parasite eggs present in the material. Frequently, it is the analysis of parasite eggs that is used to determine the presence and extent of the parasite infection or the presence of parasites in the environment. Parasite eggs can be found in many diverse places such as for example in the faecal matter of infected vertebrae hosts, in the tissues and fluids of infected vertebrae hosts, in soil, in water supplies, and on the surfaces of foodstuffs such as fruits and vegetables.

The apparatus and method can be used to analyse parasite eggs within fluid samples containing biological samples, such as faeces from vertebrate agricultural livestock or from humans. The number of parasite eggs per gram of dry matter (EPG) reveals the presence and extent of parasite infection. The EPG is determined by a variety of different processes collectively referred to as Faecal Egg Counting (FEC).

In another example, the fluid cavity of the apparatus of the invention was fabricated from a 25 mm length of 12 mm diameter PTFE rod. The fluid cavity had a 9 mm diameter and the free edge of the fluid cavity was chamfered to shape outwardly and downwardly at 45°. A projection was fabricated from a 20 mm length of 3 mm diameter borosilicate glass rod, so that the entire projection, including the contact region, was substantially fluid wettable.

The distal end of the glass rod was hemispherical. The opposing bottom end of the glass rod was a polished flat surface.

The glass rod was positioned within an aperture centrally located in the base of the fluid cavity, and the rod was located so that the apex of the hemispherical end projected approximately 2.0 mm above the edge of the fluid cavity.

The apparatus was used to analyse a sample of sheep (*Ovis aries*) faecal matter for the detection, identification and counting of the eggs of intestinal parasites. One problem with conventional methods of microscopic analysis of faecal matter is that the presence of pigments and debris in the sample causes absorbance of the visible light frequently used to illuminate the sample and limits the depth of the sample that can be analysed. However, the present invention is able to allow for the analysis of particles in relatively crude fluid samples that do not require substantial processing, such as centrifugation, prior to examination of particles using the apparatus of the invention. Therefore, the apparatus and method of the invention are able to be used in the field and are not confined to the laboratory.

Thus, when using the apparatus of the invention to analyse sheep faeces, a sample of faecal material was weighed, mixed with water and mechanically disrupted to produce a homogeneous slurry. An aliquot of the slurry was then mixed with saturated NaCl solution before filtering through a sieve that permitted the passage of particulate material of less than 1 mm in diameter.

The apparatus of the present invention was then filled with a 0.5 ml aliquot using an excess of fluid from a plastic disposable bulb pipette such that excess fluid was shed against the chamfered edge of the cavity.

The apparatus was then positioned in an optical microscope fitted with a digital camera and the image was presented on a visual display unit and electronically captured.

After waiting for the particles to equilibrate, in a single microscopic field of view the parasite eggs accumulated towards the apex of the glass rod and were counted manually on the visual display unit.

Figure 17:
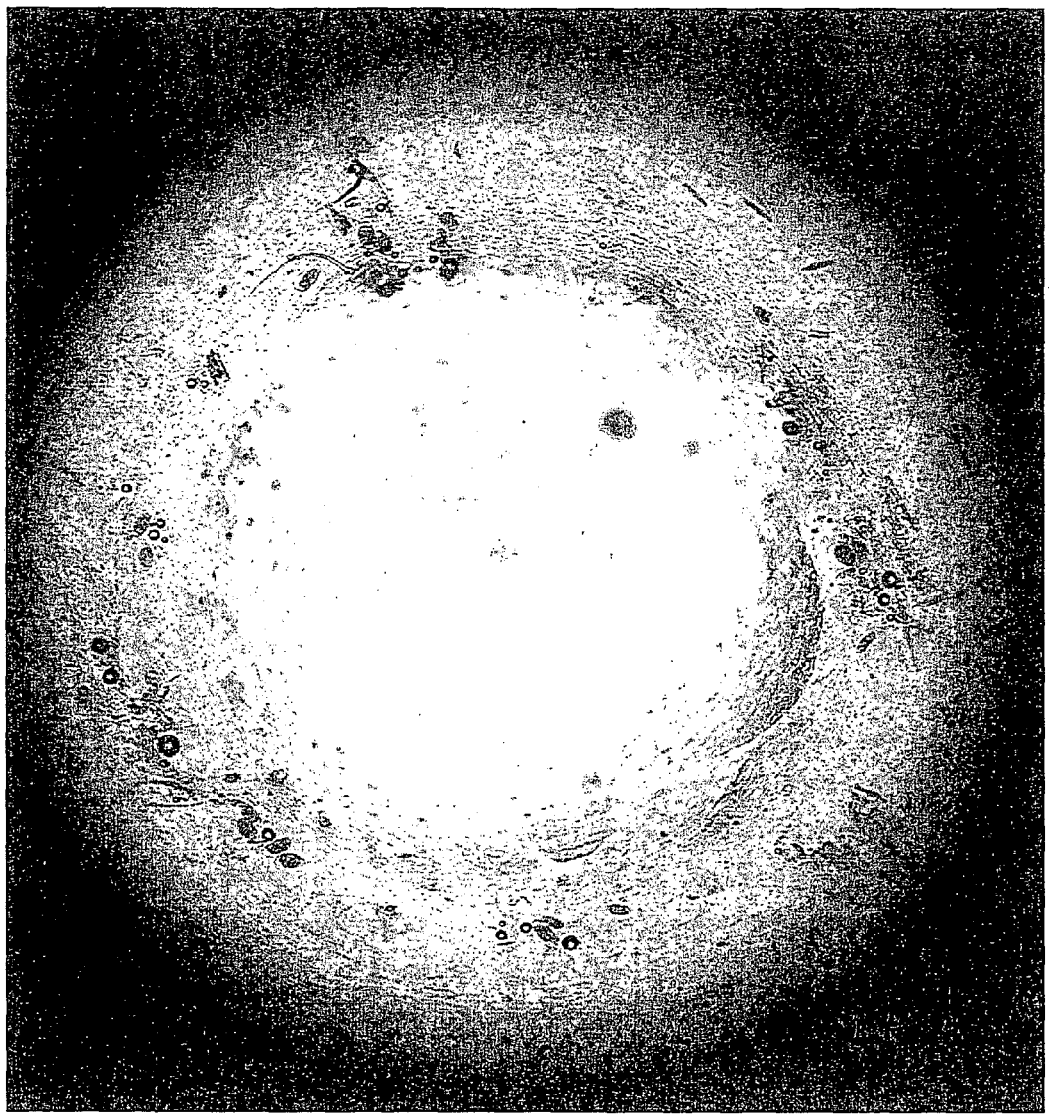
FIG. 17 shows a digital image of the apparatus of the invention when used to analyse a fluid sample containing faecal material that includes parasite eggs and other particles.

FIG. 17 is a digital image of the apparatus and fluid sample showing the accumulated parasite eggs from the fluid sample.

EXAMPLE 4

The apparatus and method of the invention were also used for analysing a sample of faecal material suspended in a dense liquid of aqueous NaCl to detect, identify, and count parasite eggs. The method included the following steps: introducing a fluid sample to the fluid cavity; waiting until the buoyant parasite eggs floated and substantially converged at the apex region of the fluid meniscus; and monitoring the apex region of the fluid meniscus, such as by microscopic examination, to procure an image of the converged parasite eggs in a single image frame to enable electronic storage and optional transmission of the image to an image display device for analysis.

The apparatus and method of the present invention was compared to the method developed by a veterinary parasite diagnostic company that utilises a modified McMaster slide for the quantitative analysis of faecal material to determine EPG.

To individual stool samples, each weighing greater than 4 gm but less than 10 gm was added 3 ml of water per gram of sample. Each sample was then separately homogenised until it was substantially free of lumps. For each specimen, an aliquot of the slurry (30 ml) was mixed with 200 ml of saturated NaCl solution. A portion of this mixture (approximately 100 ml) was filtered through a 1 mm mesh into a collection vessel, whereupon two separate samples were loaded into the modified McMaster slide. A further two samples were tested using an apparatus and method of the present invention designed to hold two separate 0.5 ml samples.

The dilution procedure, given a known mass of stool, allowed the EPG to be determined from the number of eggs enumerated in each 0.5 ml sample where each egg counted equates to 30 EPG.

In the modified McMaster slide, the analysed volume under each of the two sample grids is 0.5 ml, giving a total or 1 ml of sample read per slide. This was compared to the present invention (see Table 3).

TABLE 3

| Test number | Modified McMaster slide | | | Present Invention | | |
|---|---|---|---|---|---|---|
| | Sample 1 | Sample 2 | Average | Sample 1 | Sample 2 | Average |
| 1 | 390 | 390 | 390 | 300 | 180 | 240 |
| 2 | 330 | 330 | 330 | 480 | 450 | 465 |
| 3 | 390 | 270 | 330 | 600 | 330 | 465 |
| 4 | 540 | 330 | 435 | 480 | 540 | 510 |
| 5 | 240 | 450 | 345 | 450 | 540 | 495 |
| 6 | 270 | 390 | 330 | 330 | 450 | 390 |
| 7 | 300 | 330 | 315 | 210 | 270 | 240 |
| 8 | 300 | 360 | 330 | 180 | 330 | 255 |
| 9 | 360 | 330 | 345 | 120 | 360 | 240 |
| 10 | 420 | 420 | 420 | 180 | 240 | 210 |
| Average | 354 | 360 | 357 | 333 | 369 | 351 |

These results show a high degree of reproducibility in both the modified McMaster slide type of device and method for analysing particles and in the apparatus and method of the present invention.

The same apparatus and method of the invention can also be used to analyse parasite eggs in human faeces (which include the same or similar parasite eggs as can be found in the faeces of other animals) and in faeces from other animals including but not limited to: cats, dogs, pigs, cattle, horses, goats, poultry, birds, rats, possums, and deer.

As demonstrated above, the apparatus and method of the invention are applicable to detecting and/or identifying and/or counting a wide range of sub-millimetre scale particles, and not just pollen particles or parasite eggs. Thus, the apparatus and method of the invention may be useful for: the diagnosis of fungal, bacterial, and cellular disease; the analysis of spermatozoa in semen; the manufacturing of pharmaceuticals, dyes, inks and paints; food and beverage production; encryption; security, forensic and environmental monitoring, and the use of parasites as therapeutic agents for example.

The present invention is particularly useful for the analysis of fluid samples of single or mixed materials selected from the group comprising, but not limited to: inorganic materials; fluids; heavy fluids; liquids; heavy liquids; water; freshwater; potable water; muclolytic agents; seawater; saltwater; aqueous liquids; electrolytes; salts; sodium; chloride; glycol; glycerol; sucrose; biological materials; biological specimens; biological samples; faecal matter; urine; blood; non-biological materials; industrial materials; pharmaceutical materials; foodstuffs or honey to detect, identify or count particles suitable for the selected from the group comprising, but not limited to: air-borne particles; fluid-borne particles; granular particles; particles from biological fluids; particles from non-biological fluids; organic particles; inorganic particles; colloidal particles; dye particles; paint colloidal particles; metallic particles; semiconductor particles; quantum dot particles;

crystals; crystallites; pharmaceutical particles; contaminant particles; pathogenic particles; biological particles; cells; stem cells; oocytes; oocysts; spermatozoa; blood cells; cancer cells; spores; parasites; parasite eggs; parasite oocytes; parasite oocysts; microbes; bacteria; fungal cells; yeast cells; fungal spores; lipoproteins; liposomes; particles conjugated to particles; particles conjugated to molecules; particles conjugated to dyes; particles conjugated to fluorescent molecules or particles conjugated to fluorescence quenching molecules.

However, references herein to specific examples of materials analysis should not be interpreted in any way as limiting the scope of the present invention which, is applicable to detecting identifying and counting of a wide range of sub-millimetre scale particles with industrial applicability that includes but is not limited to: the diagnosis of fungal, bacterial and cellular disease; the analysis of spermatozoa in semen; the manufacturing of pharmaceuticals, dyes, inks and paints; food and beverage production; encryption; security, forensic, environmental monitoring, petrological and archaeological analysis.

It will be apparent to those skilled in the art that an important feature of the present invention is the provision of a projection to cause buoyant particles to ascend in a dense fluid sample and accumulate at the highest point of the fluid sample, which will be located either at the surface of the contact region at the sides of the projection or located above the projection.

Advantages

The apparatus and method of the invention offer a fast and simple way to detect, identify, and count particles in a fluid sample. The invention allows particles to accumulate in one area so that the particles can be seen in a single microscopic field of view. This allows for simple recordal of images of the fluid sample to be captured and stored as a permanent record for future reference and auditing. The fluid sample can also be illuminated to analyse particles, even where the fluid sample is heavily pigmented or where it includes debris.

It will be appreciated that the examples and embodiments given above are non-limiting in their scope and that variations combining one or more features of the above-described examples and embodiments can also be used in other embodiments of the invention.

Various embodiments of the invention have been described by way of example only. Variations and modifications may be made to the embodiments, as would be apparent to those skilled in the art, without departing from the scope of the invention. It is, therefore, intended that such variations and modifications are included within the scope of the invention. Furthermore, where known equivalents to specific features exist, such equivalents are incorporated as if specifically referred in this specification.

What we claim is:

1. A portable sample holder including:
   a. a portable base defining a fluid cavity of less than 15 mm in diameter; and
   b. a projection extending from the base having a hydrophillic tapered portion extending above the fluid cavity, wherein the tapered portion is configured so that when a sample solution is introduced into the sample holder a meniscus forms having its apex in contact with the tapered portion which promotes the migration of particles in the sample fluid to a region proximate the tapered portion and wherein the taper portion extends above the fluid cavity less than approximately 2 mm.

2. The sample holder according to claim 1, wherein the surface of at least the tapered portion of the projection exhibits properties that make it superhydrophilic, oleophilic, or fluorophilic.

3. An apparatus for observing particales incuding the sample holder according to claim 1 and a light source to illuminate at least a portion of a fluid sample held by the sample holder when the apparatus is in use.

4. The apparatus according to claim 3, wherein the light source is below the projection and the projection provides a light transmitting conduit to illuminate at least a portion of a fluid sample held by the sample holder when the apparatus is in use.

5. An apparatus for observing particles including the sample holder according to claim 1 and an optical instrument for observing a fluid sample held by the sample holder when the apparatus is in use.

6. The apparatus according to claim 5, wherein the optical instrument is an image sensor.

7. The apparatus of claim 6 wherein the image sensor is positioned above the sample holder.

8. The apparatus of claim 6 wherein the image sensor is positioned below the sample holder.

9. The apparatus according to claim 8, wherein the projection includes a plurality of fibre optic cables coupled to the optical sensor.

10. The sample holder according to claim 1 wherein at least part of the surface of the tapered portion is textured.

11. The sample holder according to claim 1, wherein the tapered portion is conical, hemispherical, stepped or frusto-conical.

12. The sample holder according to claim 2, wherein the tapered portion is transparent.

13. The sample holder according to claim 1, wherein the sample holder further comprises a wall or walls extending from the base.

14. The sample holder according to claim 13 wherein the base and wall(s) together form a fluid cavity and the projection is positioned generally centrally within the fluid cavity.

15. The sample holder according to claim 14, wherein the wall(s) of the fluid cavity terminate in a free edge, which is chamfered to form a surface that slopes outwardly toward the base of the sample holder.

16. The sample holder according to claim 14, wherein the base of the fluid cavity is substantially concave.

17. The sample holder according to claim 14 wherein the wall(s) comprise inner surfaces facing the fluid cavity, the inner surfaces of the wall(s) exhibiting properties that cause the wall(s) to substantially repel a fluid sample when the apparatus is in use so that the fluid sample forms a meniscus having its apex in contact with the projection.

18. The sample holder according to claim 14 wherein the inner surfaces of the walls are hydrophobic; super-hydrophobic; oleophobic; fluorophobic; ionic; cationic or anionic.

19. A portable sample holder including:
   a base having a fluid cavity with side walls spaced apart less than 15 mm; and
   a projection having a tapered portion, the projection having a width of less than 5mm and extending from the base above the side walls, wherein the tapered portion is configured so that when a sample solution is introduced into the sample holder a meniscus forms having its apex in contact with the tapered portion which promotes the migration of particles in the sample fluid to a region proximate the tapered portion and wherein the taper portion extends above the fluid cavity less than approximately 2 mm.

* * * * *

UNITED STATES PATENT AND TRADEMARK OFFICE
CERTIFICATE OF CORRECTION

| | |
|---|---|
| PATENT NO. | : 8,961,907 B2 |
| APPLICATION NO. | : 13/387076 |
| DATED | : February 24, 2015 |
| INVENTOR(S) | : Stephen John Sowerby |

It is certified that error appears in the above-identified patent and that said Letters Patent is hereby corrected as shown below:

In the Claims,

Column 26, Claim 3, line 5, delete "particales incuding" and insert --particles including--.

Column 26, Claim 12, line 29, delete "claim 2" and insert --claim 1--.

Signed and Sealed this
Third Day of November, 2015

Michelle K. Lee
*Director of the United States Patent and Trademark Office*